US010716944B2

(12) United States Patent
Haasl et al.

(10) Patent No.: US 10,716,944 B2
(45) Date of Patent: Jul. 21, 2020

(54) SYSTEMS AND METHODS FOR TREATING CARDIAC ARRHYTHMIAS

(71) Applicant: CARDIAC PACEMAKERS, INC., St. Paul, MN (US)

(72) Inventors: Benjamin J. Haasl, Forest Lake, MN (US); Lili Liu, Maple Grove, MN (US); Allan Charles Shuros, St. Paul, MN (US)

(73) Assignee: CARDIAC PACEMAKERS, INC., St. Paul, MN (US)

( * ) Notice: Subject to any disclaimer, the term of this patent is extended or adjusted under 35 U.S.C. 154(b) by 204 days.

(21) Appl. No.: 15/925,247

(22) Filed: Mar. 19, 2018

(65) Prior Publication Data

US 2018/0264262 A1 Sep. 20, 2018

Related U.S. Application Data

(60) Provisional application No. 62/473,711, filed on Mar. 20, 2017.

(51) Int. Cl.
*A61N 1/375* (2006.01)
*A61N 1/368* (2006.01)
(Continued)

(52) U.S. Cl.
CPC .......... *A61N 1/368* (2013.01); *A61N 1/3756* (2013.01); *A61N 1/057* (2013.01); *A61N 1/3956* (2013.01)

(58) Field of Classification Search
CPC ...... A61N 1/057; A61N 1/368; A61N 1/3756; A61N 1/3956
See application file for complete search history.

(56) References Cited

U.S. PATENT DOCUMENTS 5,170,802 A  12/1992  Mehra
5,238,004 A   8/1993  Sahatjian et al.
(Continued)

FOREIGN PATENT DOCUMENTS

WO   2016010958 A1   1/2016
WO   2016011042 A1   1/2016
(Continued)

OTHER PUBLICATIONS

International Search Report and Written Opinion dated May 24, 2018 for International Application No. PCT/US2018/023121.
(Continued)

*Primary Examiner* — George Manuel
(74) *Attorney, Agent, or Firm* — Seager, Tufte & Wickhem LLP

(57) ABSTRACT

A leadless pacing device may include a housing, a distal extension extending distally of a distal end of the housing, one or more electrodes supported by the housing, a distal electrode supported by the distal extension, and a processing module located within an interior space of the housing and electrically coupled to the one or more electrodes supported by the housing and the distal electrode supported by the distal extension. The housing may be positioned within a coronary sinus and the distal extension may be positioned within a vessel extending from the coronary sinus. The processing module may determine whether cardiac events occurred based on near-field signals and/or far-field signals sensed using the one or more electrodes supported by the housing and the distal electrode. The processing module may generate cardiac stimulation pulses based on the determination of whether a cardiac event occurred and where it occurred.

20 Claims, 22 Drawing Sheets

(51) Int. Cl.
    *A61N 1/39*     (2006.01)
    *A61N 1/05*     (2006.01)

(56) References Cited

U.S. PATENT DOCUMENTS

| | | |
|---|---|---|
| 5,540,236 A | 7/1996 | Ginn |
| 5,803,928 A | 9/1998 | Tockman et al. |
| 5,925,073 A | 7/1999 | Chastain et al. |
| 6,070,104 A | 5/2000 | Hine et al. |
| 6,445,953 B1 | 9/2002 | Bulkes et al. |
| 6,508,803 B1 | 1/2003 | Horikawa et al. |
| 6,584,362 B1 | 6/2003 | Scheiner et al. |
| 6,592,518 B2 | 7/2003 | Denker et al. |
| 6,907,285 B2 | 6/2005 | Denker et al. |
| 7,003,350 B2 | 2/2006 | Denker et al. |
| 7,082,336 B2 | 7/2006 | Ransbury et al. |
| 7,236,821 B2 | 6/2007 | Cates et al. |
| 7,295,879 B2 | 11/2007 | Denker et al. |
| 7,310,556 B2 | 12/2007 | Bulkes |
| 7,519,421 B2 | 4/2009 | Denker et al. |
| 7,529,589 B2 | 5/2009 | Williams et al. |
| 7,535,296 B2 | 5/2009 | Bulkes et al. |
| 7,617,007 B2 | 11/2009 | Williams et al. |
| 7,711,434 B2 | 5/2010 | Denker et al. |
| 7,734,343 B2 | 6/2010 | Ransbury et al. |
| 7,749,265 B2 | 7/2010 | Denker et al. |
| 7,769,466 B2 | 8/2010 | Denker et al. |
| 7,826,903 B2 | 11/2010 | Denker et al. |
| 7,840,282 B2 | 11/2010 | Williams et al. |
| 7,894,915 B1 | 2/2011 | Chitre et al. |
| 7,899,554 B2 | 3/2011 | Williams et al. |
| 8,050,775 B2 | 11/2011 | Westlund et al. |
| 8,103,359 B2 | 1/2012 | Reddy |
| 8,116,883 B2 | 2/2012 | Williams et al. |
| 8,160,722 B2 | 4/2012 | Ruffen et al. |
| 8,204,596 B2 | 6/2012 | Ransbury et al. |
| 8,239,045 B2 | 8/2012 | Ransbury et al. |
| 8,311,633 B2 | 11/2012 | Ransbury et al. |
| 8,489,205 B2 | 7/2013 | Stotts et al. |
| 8,527,068 B2 | 9/2013 | Ostroff |
| 8,571,678 B2 | 10/2013 | Wang |
| 8,630,710 B2 | 1/2014 | Kumar et al. |
| 8,634,912 B2 | 1/2014 | Bomzin et al. |
| 8,634,919 B1 | 1/2014 | Hou et al. |
| 8,644,934 B2 | 2/2014 | Hastings et al. |
| 8,670,824 B2 | 3/2014 | Anderson et al. |
| 8,670,842 B1 | 3/2014 | Bomzin et al. |
| 8,700,181 B2 | 4/2014 | Bomzin et al. |
| 8,758,365 B2 | 6/2014 | Bonner et al. |
| 8,781,605 B2 | 7/2014 | Bomzin et al. |
| 8,798,740 B2 | 8/2014 | Samade et al. |
| 8,798,770 B2 | 8/2014 | Reddy |
| 8,886,340 B2 | 11/2014 | Williams et al. |
| 8,914,131 B2 | 12/2014 | Bomzin et al. |
| 8,938,294 B2 | 1/2015 | Anderson et al. |
| 8,989,873 B2 | 3/2015 | Locsin |
| 8,996,109 B2 | 3/2015 | Karst et al. |
| 9,008,777 B2 | 4/2015 | Dianaty et al. |
| 9,168,372 B2 | 10/2015 | Fain |
| 9,265,962 B2 | 2/2016 | Dianaty et al. |
| 9,278,218 B2 | 3/2016 | Karst et al. |
| 9,289,612 B1 | 3/2016 | Sambelashvili et al. |
| 9,339,646 B2 | 5/2016 | Ollivier |
| 9,399,140 B2 | 7/2016 | Cho et al. |
| 9,446,248 B2 | 9/2016 | Sheldon et al. |
| 9,468,755 B2 | 10/2016 | Westlund et al. |
| 9,526,891 B2 | 12/2016 | Eggen et al. |
| 9,539,423 B2 | 1/2017 | Bonner et al. |
| 9,669,223 B2 | 6/2017 | Auricchio et al. |
| 9,827,426 B2 | 11/2017 | Reddy |
| 2006/0241732 A1 | 10/2006 | Denker et al. |
| 2007/0106357 A1 | 5/2007 | Denker et al. |
| 2013/0023975 A1 | 1/2013 | Locsin |
| 2013/0035748 A1 | 2/2013 | Bonner et al. |
| 2013/0110127 A1 | 5/2013 | Bomzin et al. |
| 2013/0110219 A1 | 5/2013 | Bomzin et al. |
| 2013/0116529 A1 | 5/2013 | Min et al. |
| 2013/0116738 A1 | 5/2013 | Samade et al. |
| 2013/0116740 A1 | 5/2013 | Bomzin et al. |
| 2013/0116741 A1 | 5/2013 | Bomzin et al. |
| 2013/0123872 A1 | 5/2013 | Bomzin et al. |
| 2013/0138006 A1 | 5/2013 | Bomzin et al. |
| 2013/0253342 A1 | 9/2013 | Griswold et al. |
| 2013/0325081 A1 | 12/2013 | Karst et al. |
| 2013/0345770 A1 | 12/2013 | Dianaty et al. |
| 2014/0100627 A1 | 4/2014 | Min |
| 2014/0107723 A1 | 4/2014 | Hou et al. |
| 2014/0172034 A1 | 6/2014 | Bomzin et al. |
| 2014/0172060 A1 | 6/2014 | Bomzin et al. |
| 2014/0243848 A1 | 8/2014 | Auricchio et al. |
| 2014/0288576 A1 | 9/2014 | Bomzin et al. |
| 2015/0088219 A1* | 3/2015 | Nuta .................. A61N 1/37288 607/17 |
| 2016/0015287 A1 | 1/2016 | Anderson et al. |
| 2016/0015322 A1 | 1/2016 | Anderson et al. |
| 2016/0059003 A1 | 3/2016 | Eggen et al. |
| 2016/0082270 A1 | 3/2016 | Mothilal et al. |
| 2016/0129239 A1 | 5/2016 | Anderson |
| 2016/0158561 A1 | 6/2016 | Reddy |
| 2016/0228712 A1 | 8/2016 | Koop |
| 2016/0310703 A1 | 10/2016 | Drake et al. |
| 2016/0310723 A1 | 10/2016 | Eggen et al. |
| 2016/0310726 A1 | 10/2016 | Demmer et al. |
| 2017/0028194 A1 | 2/2017 | Bonner et al. |
| 2017/0326355 A1 | 11/2017 | Koop et al. |

FOREIGN PATENT DOCUMENTS

| | | |
|---|---|---|
| WO | 2016126465 A1 | 8/2016 |
| WO | 2016172106 A1 | 10/2016 |

OTHER PUBLICATIONS

International Search Report and Written Opinion dated May 30, 2018 for International Application No. PCT/US2018/023130.

* cited by examiner

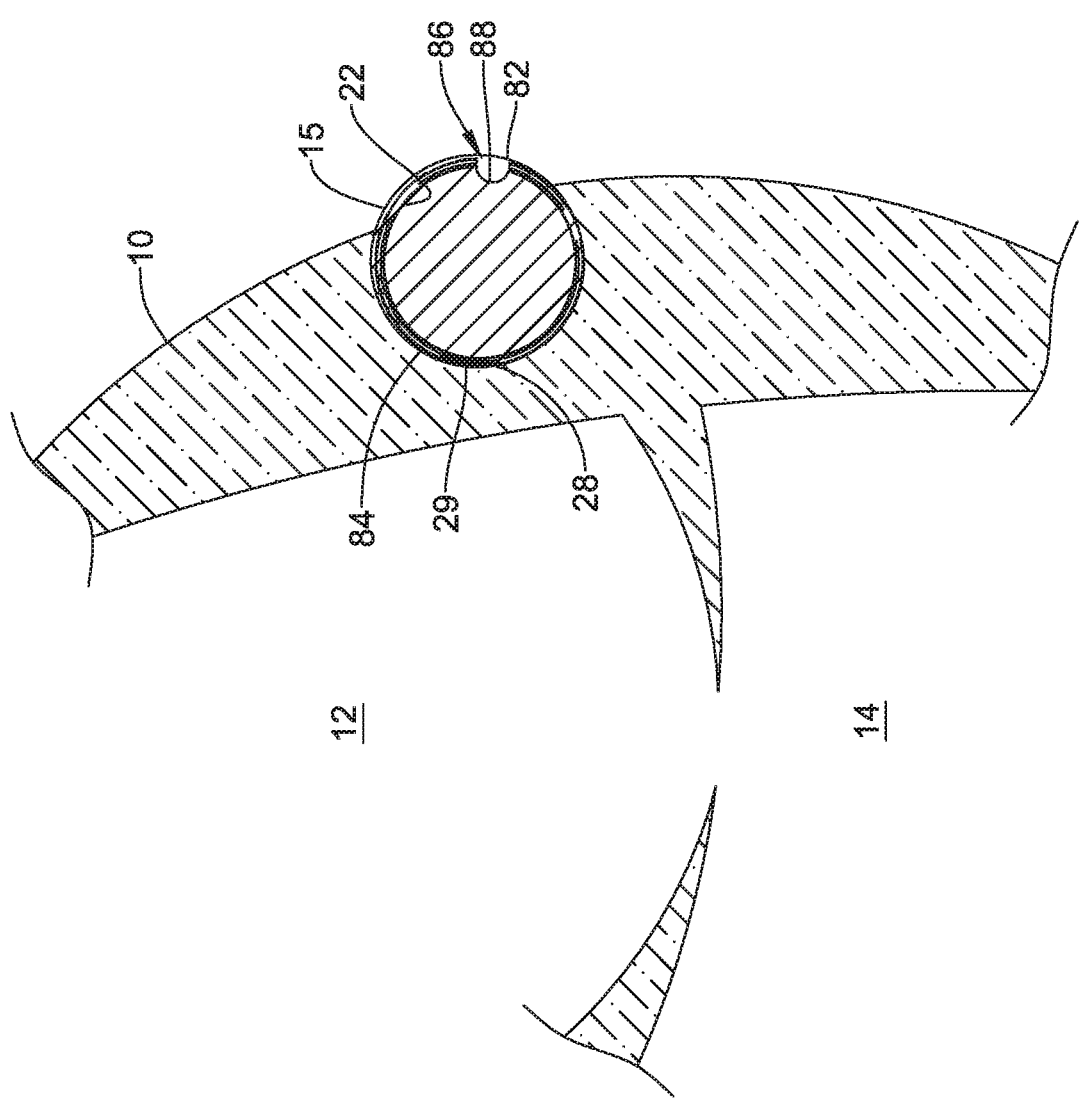

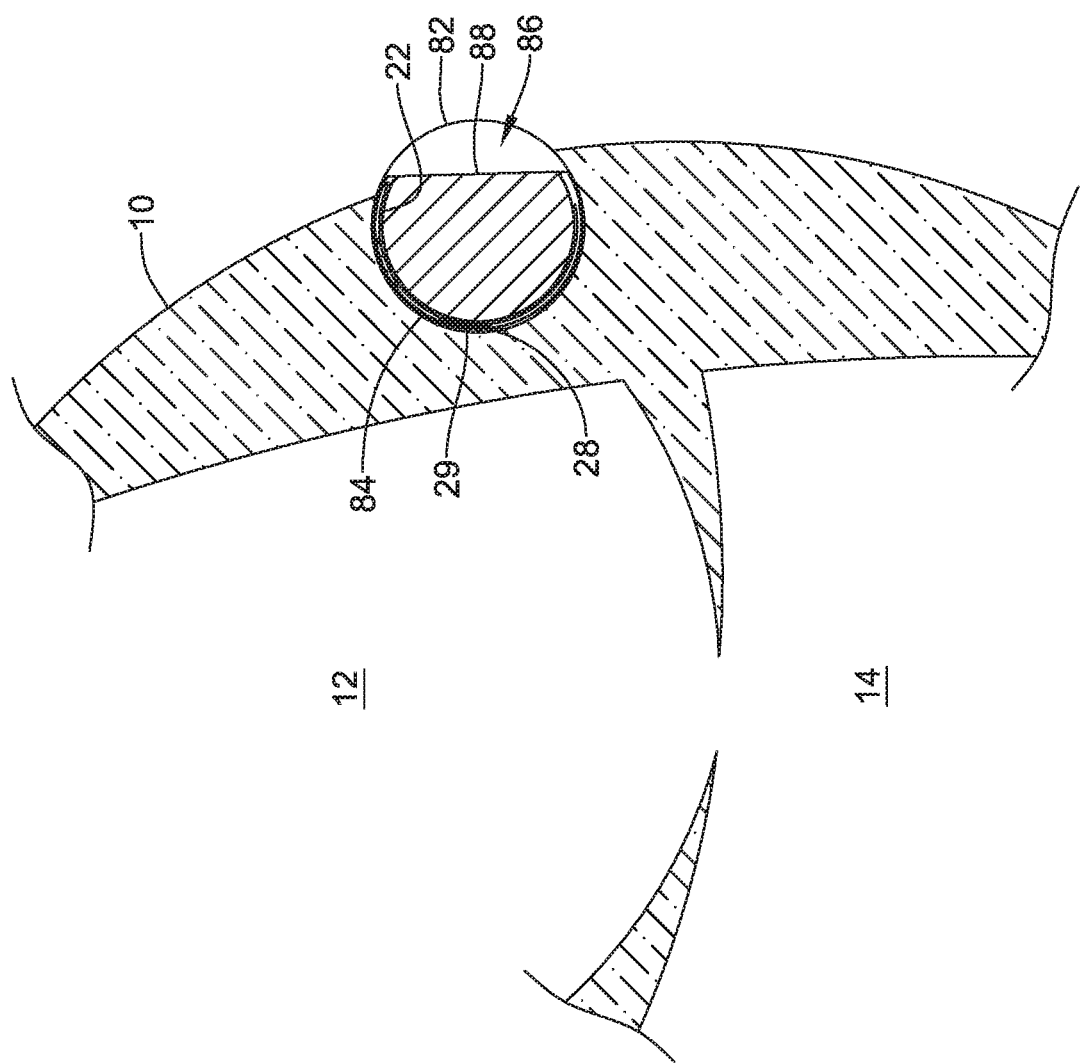

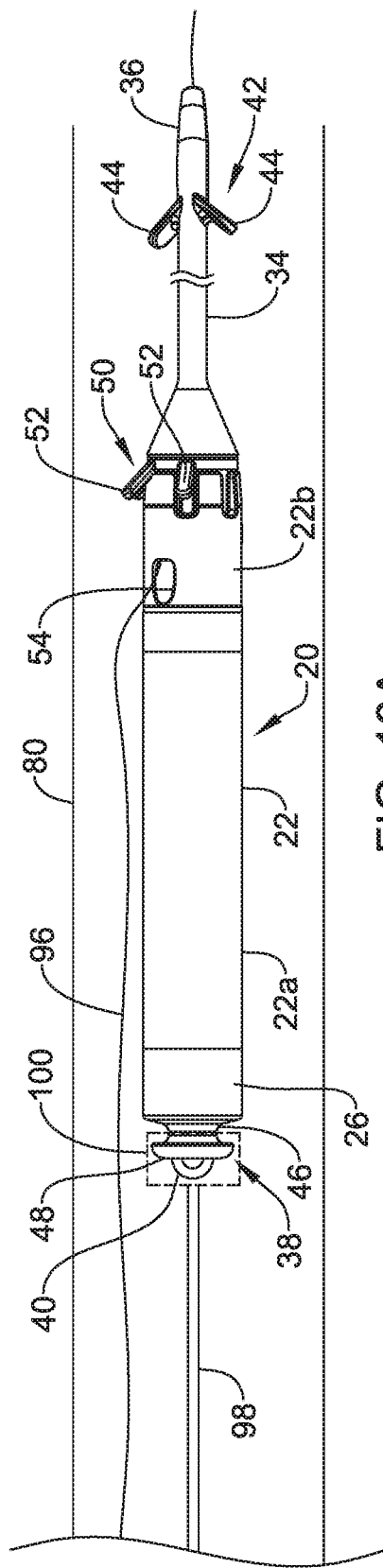
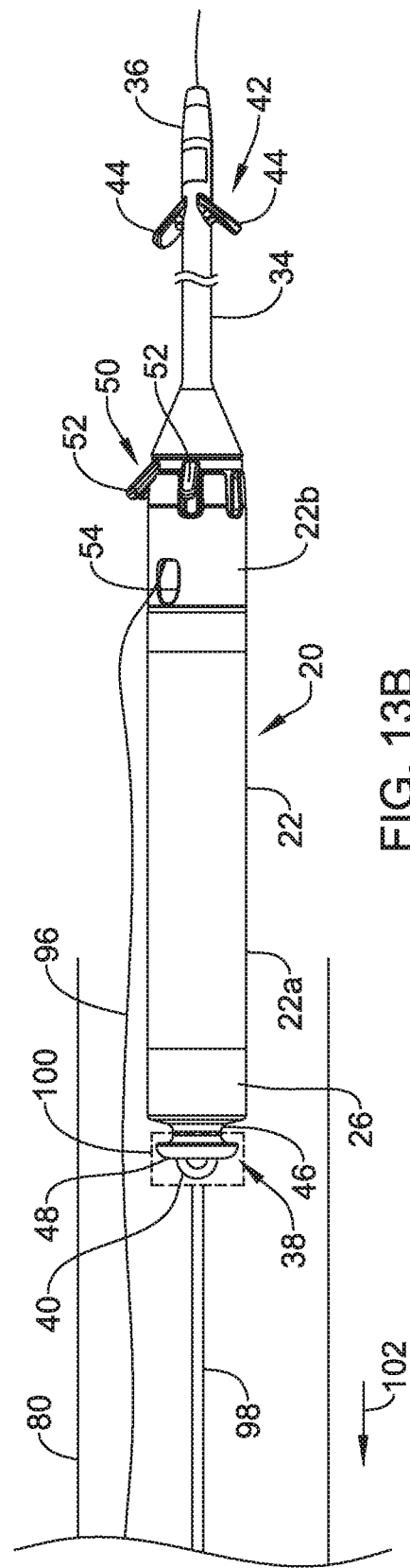
FIG. 13A
FIG. 13B

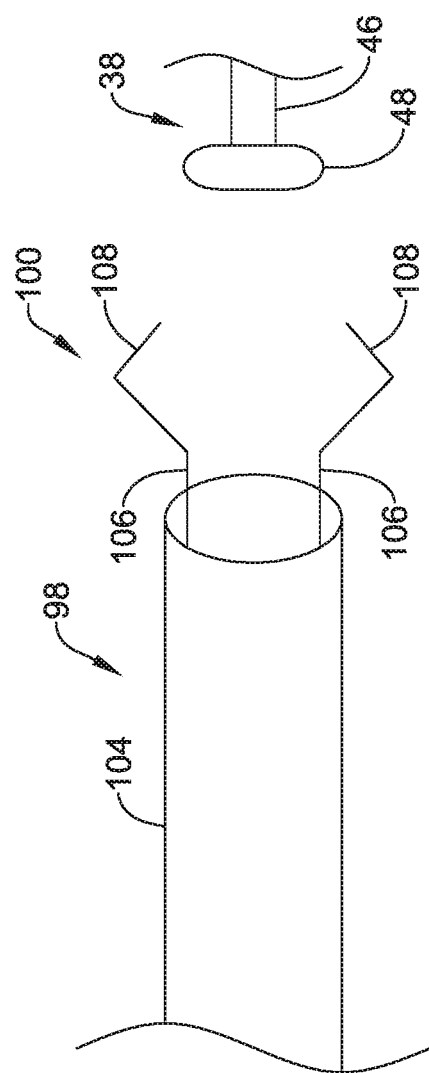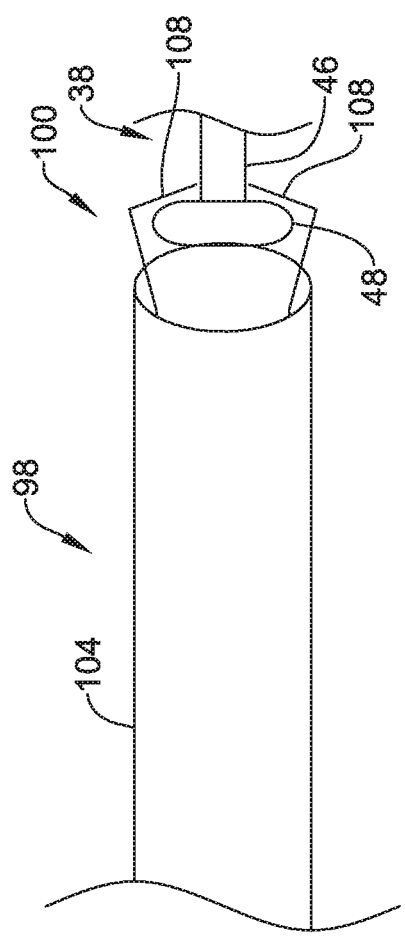

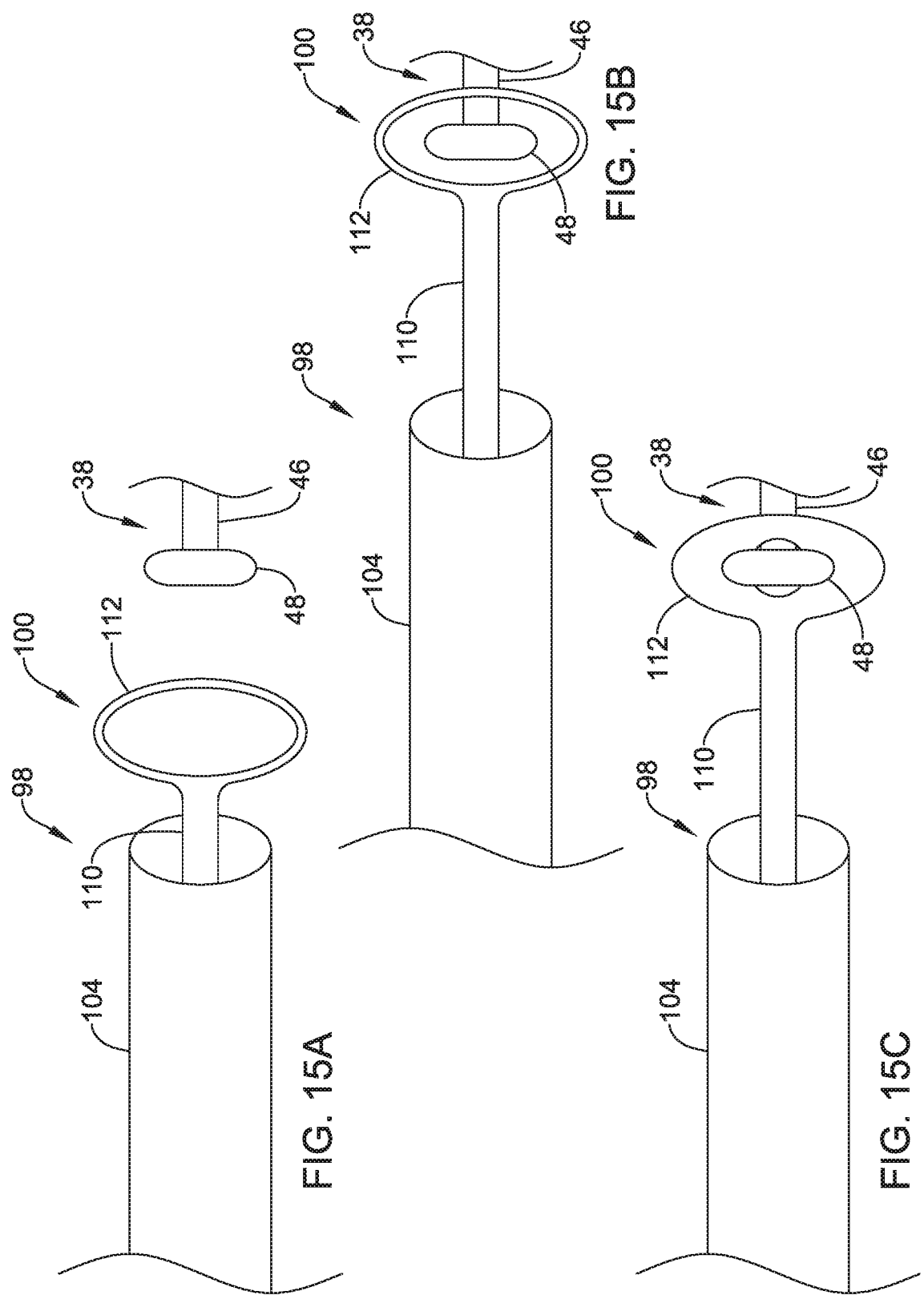

SYSTEMS AND METHODS FOR TREATING CARDIAC ARRHYTHMIAS

CROSS REFERENCE TO RELATED APPLICATIONS

The present application claims the benefit of and priority to U.S. Provisional Patent Application Ser. No. 62/473,711, filed Mar. 20, 2017, the disclosure of which is incorporated herein by reference.

TECHNICAL FIELD

The present disclosure pertains to medical devices, and methods for manufacturing and/or using medical devices. More particularly, the present disclosure pertains to leadless cardiac devices and methods, such as leadless pacing devices and methods, and delivery devices and methods for such leadless devices.

BACKGROUND

A wide variety of medical devices have been developed for medical use, for example, cardiac use. Some of these devices include catheters, leads, pacemakers, and the like, and delivery devices and/or systems used for delivering such devices. These devices are manufactured by any one of a variety of different manufacturing methods and may be used according to any one of a variety of methods. Of the known medical devices, delivery systems, and methods, each has certain advantages and disadvantages. There is an ongoing need to provide alternative medical devices and delivery devices as well as alternative methods for manufacturing and using medical devices and delivery devices.

SUMMARY

This disclosure provides design, material, manufacturing method, and use alternatives for medical devices, including cardiac sensing and pacing devices and delivery devices.

In a first example, a leadless pacing device may comprise a housing configured to be positioned within a coronary sinus, a distal extension extending distally of a distal end of the housing, the distal extension is configured to be positioned within a vessel extending from the coronary sinus, an electrode supported by the housing, a distal electrode supported by the distal extension, and a processing module located within an interior space of the housing and electrically coupled to the electrode supported by the housing and the distal electrode supported by the distal extension, wherein the processing module may be configured to determine whether an atrial event occurred based on near-field signals sensed using the electrode supported by the housing, and determine whether a ventricular event occurred based on near-field signals sensed using the distal electrode.

Alternatively or additionally to any of the examples above, in another example, the processing module may be configured to generate a cardiac stimulation pulse based on the determination of whether an atrial event occurred and the determination of whether a ventricular event occurred.

Alternatively or additionally to any of the examples above, in another example, the generated cardiac stimulation pulse may be generated through the electrode supported by the housing.

Alternatively or additionally to any of the examples above, in another example, the generated cardiac stimulation pulse may be generated through the distal electrode.

Alternatively or additionally to any of the examples above, in another example, the processing module may be configured to determine whether a ventricular event occurred based on far-field signals sensed using the electrode supported by the housing.

Alternatively or additionally to any of the examples above, in another example, the processing module may determine whether an atrial event occurred in a right atrium of a patient's heart based on near-field sensing signals sensed using the electrode supported by the housing.

Alternatively or additionally to any of the examples above, in another example, the processing module may determine whether an atrial event occurred in a left atrium of a patient's heart based on near-field sensing signals sensed using the electrode supported by the housing.

Alternatively or additionally to any of the examples above, in another example, the electrode supported by the housing may be a first electrode and the leadless pacing device may further comprise a second electrode supported by the housing.

Alternatively or additionally to any of the examples above, in another example, the processing module may be configured to determine whether an atrial event occurred based on near-field signals sensed using the second electrode.

Alternatively or additionally to any of the examples above, in another example, the processing module may be configured to determine whether an atrial event occurred in a right atrium of a patient's heart based on near-field signals sensed using the first electrode and determine whether an atrial event occurred in a left atrium of the patient's heart based on near-field sensing signal sensed using the second electrode.

Alternatively or additionally to any of the examples above, in another example, the first electrode may be a bipolar electrode and the second electrode may be a bipolar electrode.

Alternatively or additionally to any of the examples above, in another example, the distal extension may support a plurality of electrodes.

Alternatively or additionally to any of the examples above, in another example, the plurality of electrodes supported by the distal extension may comprise a first ring electrode at a distal end of the distal extension and a second ring electrode spaced proximally of the first ring electrode.

In another example, a leadless pacing device may comprise a housing configured to be positioned within a coronary sinus, a distal extension connected to a distal end of the housing and extending distally of the housing, a lumen extending through the distal extension to a distal guide wire port, a first electrode supported by a proximal end of the housing, a second electrode supported by a distal end of the housing, a proximal guide wire port forming a proximal end of the lumen and extending through a side of the housing at a location between the first electrode and the second electrode, a third electrode supported by the distal extension, and a processing module located within an interior space of the housing and electrically coupled to the first electrode, the second electrode, and the third electrode, wherein the processing module may be configured to determine whether an atrial event occurred based on near-field signals sensed using one or both of the first electrode and the second electrode, and determine whether a ventricular event occurred based on near-field signals sensed using the third electrode.

Alternatively or additionally to any of the examples above, in another example, the processing module may be configured to generate a cardiac stimulation pulse based on the determination of whether an atrial event occurred and the determination of whether a ventricular event occurred.

Alternatively or additionally to any of the examples above, in another example, the processing module may be configured to determine whether a ventricular event occurred based on far-field signals sensed using one or both of the first electrode and the second electrode.

In a further example, a method of using a leadless pacing device may comprise sensing near-field signals of an atrium of a patient's heart using an electrode supported by a housing of a leadless pacing device located in a coronary sinus of the patient's heart, sensing near-field signals of a ventricle of the patient's heart using a distal electrode supported by a distal extension of a leadless pacing device located in a vessel extending from the coronary sinus, identifying an atrial cardiac event based on the near-field signals sensed by the electrode supported by the housing, and identifying a ventricle cardiac event based on the near-field signals sensed by the distal electrode.

Alternatively or additionally to any of the examples above, in another example, the method may further comprise generating a cardiac stimulation pulse based on one or both of the identified atrial cardiac event and the identified ventricle cardiac event.

Alternatively or additionally to any of the examples above, in another example, the method may further comprise sensing far-field signals of a ventricle of the patient's heart using the electrode supported by the housing of the leadless pacing device located in the coronary sinus of the patient's heart, and identifying a ventricle cardiac event based on the far-field signals sensed by the electrode supported by the housing.

Alternatively or additionally to any of the examples above, in another example, wherein the electrode supported by the housing is a first electrode, the method may further comprise sensing near-field signals of an atrium of a patient's heart using a second electrode supported by the housing of the leadless pacing device located in the coronary sinus of the patient's heart, and identifying if an atrial cardiac event occurred in a right atrium or a left atrium of a patient's heart based on near-field signals sensed by one or both of the first electrode and the second electrode.

The above summary of some embodiments is not intended to describe each disclosed embodiment or every implementation of the present disclosure. The Figures, and Detailed Description, which follow, more particularly exemplify some of these embodiments.

BRIEF DESCRIPTION OF THE DRAWINGS

The disclosure may be more completely understood in consideration of the following detailed description in connection with the accompanying drawings, in which:

FIGS. 8A and 8B are schematic diagrams of an example implantable leadless pacing device in a heart;

FIGS. 13A and 13B are schematic diagrams showing an example implantable leadless pacing device being pushed along a guide wire and out the distal end of a guide catheter;

FIGS. 14A and 14B are schematic diagrams of an example interlocking mechanism for engaging and/or disengaging a proximal member of an implantable leadless pacing device;

FIGS. 15A-15C are schematic diagrams of an example interlocking mechanism for engaging and/or disengaging a proximal member of an implantable leadless pacing device;

Figure 1:
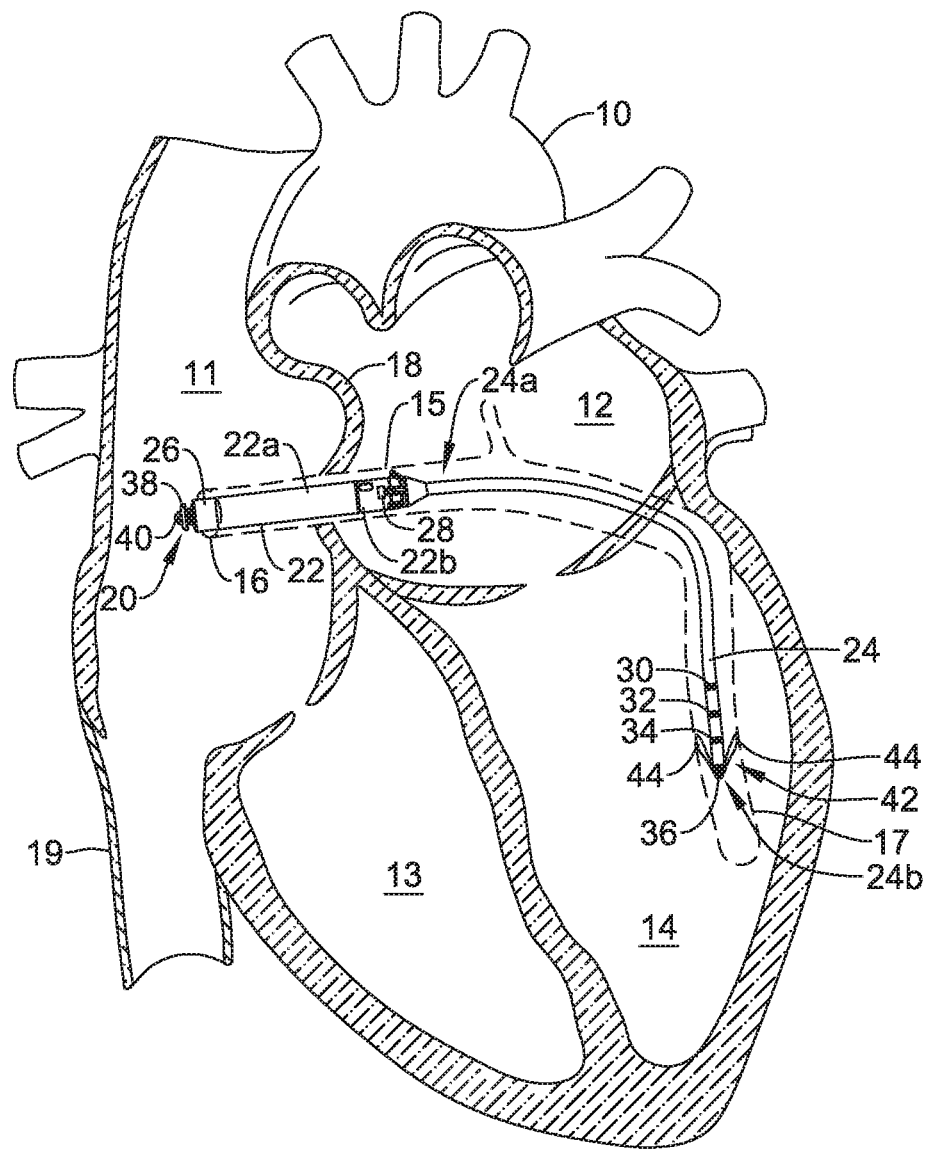
FIG. 1 is a schematic diagram of an example leadless pacing device implanted within a heart.

While the disclosure is amenable to various modifications and alternative forms, specifics thereof have been shown by way of example in the drawings and will be described in detail. It should be understood, however, that the intention is not to limit aspects of the disclosure to the particular embodiments described. On the contrary, the intention is to cover all modifications, equivalents, and alternatives falling within the spirit and scope of the disclosure.

DETAILED DESCRIPTION

For the following defined terms, these definitions shall be applied, unless a different definition is given in the claims or elsewhere in this specification.

All numeric values are herein assumed to be modified by the term "about," whether or not explicitly indicated. The term "about" generally refers to a range of numbers that one of skill in the art would consider equivalent to the recited value (i.e., having the same function or result). In many instances, the terms "about" may include numbers that are rounded to the nearest significant figure.

The recitation of numerical ranges by endpoints includes all numbers within that range (e.g., 1 to 5 includes 1, 1.5, 2, 2.75, 3, 3.80, 4, and 5).

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

It is noted that references in the specification to "an embodiment", "some embodiments", "other embodiments", etc., indicate that the embodiment described may include one or more particular features, structures, and/or characteristics. However, such recitations do not necessarily mean that all embodiments include the particular features, structures, and/or characteristics. Additionally, when particular features, structures, and/or characteristics are described in connection with one embodiment, it should be understood that such features, structures, and/or characteristics may also be used connection with other embodiments whether or not explicitly described unless clearly stated to the contrary.

The following detailed description should be read with reference to the drawings in which similar structures in different drawings are numbered the same. The drawings, which are not necessarily to scale, depict illustrative embodiments and are not intended to limit the scope of the disclosure.

The following description should be read with reference to the drawings in which similar elements in different drawings are numbered the same. The description and the drawings, which are not necessarily to scale, depict illustrative embodiments and are not intended to limit the scope of the disclosure.

Cardiac pacemakers provide electrical stimulation to heart tissue to cause the heart to contract and thus pump blood through the vascular system. Conventional pacemakers typically include an electrical lead that extends from a pulse generator implanted subcutaneously or sub-muscularly to an electrode positioned adjacent the inside or outside wall of the cardiac chamber. As an alternative to conventional pacemakers, self-contained or leadless cardiac pacemakers have been proposed. Leadless cardiac pacemakers are small capsules typically fixed to an intracardiac implant site in or around a cardiac chamber. The small capsule typically includes bipolar pacing/sensing electrodes, a power source (e.g., a battery), and associated electrical circuitry for controlling the pacing/sensing electrodes, and thus provide electrical stimulation to heart tissue and/or sense a physiological condition. In some cases, the leadless cardiac pacemakers may include a proximal and/or a distal extension extending from the small capsule, where the extension(s) may include one or more pacing/sensing electrodes. The capsule may be delivered to the heart using a delivery device which may be advanced through a femoral vein, into the inferior vena cava, into the right atrium, and into the coronary sinus and vessels extending through and/or to the coronary sinus. Accordingly, it may be desirable to provide cardiac pacing devices and delivery devices which facilitate advancement through the vasculature.

The leadless pacing device described herein may detect and treat cardiac arrhythmias, and more particularly, deliver electrical stimulation therapy to a right atrium, left atrium, right atrium, and/or a left ventricle of a heart of a patient. For instance, one or more devices may be implanted on or within a patient's heart, and the one or more devices may be configured to deliver electrical stimulation therapy to one or more chambers of the patient's heart in accordance with one or more therapy programs and/or to treat one or more types of detected cardiac arrhythmias. Some example electrical stimulation therapies include bradycardia therapy, cardiac resynchronization therapy (CRT), anti-tachycardia pacing (ATP) therapy, defibrillation and/or cardioversion therapy, and the like. Some example cardiac arrhythmias include atrial fibrillation or atrial flutter, ventricular fibrillation, and tachycardia.

FIG. 1 is a conceptual diagram of an illustrative system for delivering electrical stimulation therapy to a patient's heart, including delivering electrical stimulation therapy to a right atrium, left atrium, right atrium, and/or a left ventricle of the patient's heart. FIG. 1 shows an illustrative leadless pacing device 20 implanted in and around heart 10. Heart 10 of FIG. 1 is depicted showing a right atrium 11, a left atrium 12, a right ventricle 13, a left ventricle 14, a coronary sinus 15, a coronary sinus ostium 16, a great cardiac vein 17, and a septum 18.

In the example of FIG. 1, the leadless pacing device 20 includes a housing 22 having a proximal end and a distal end and a distal extension 24 extending distally of the distal end of the housing 22. However, in some instances, the distal extension 24 may not be included and/or one or more other distal and/or proximal extension may be included. The housing 22 may be a single portion or may have a first portion 22a (e.g., a can or body), a second portion 22b (e.g., a head or molded portion), and/or one or more other portions. It is contemplated that the housing 22 need not have the same cross sectional shape along its entire length. When implanted, the housing 22 may be fully or partially disposed within coronary sinus 15 of the patient's heart 10, while the distal extension 24 may be fully or partially disposed within a vessel extending from the coronary sinus 15 (e.g., the great cardiac vein 17, an anterior interventricular vein, and/or other laterally descending vessel).

The housing 22 may have any dimension suitable for implantation at a target location within the heart 10 of a patient. In one example, the housing 22 may have a cross-section diameter or area sufficient to fit within coronary sinus 15. Sizes of coronary sinus 15 may vary in humans between about 0.12 inches (3 mm) to about 0.6 inches (15 mm). A diameter of the housing 22 may range, in different embodiments, between about 0.1 inches (2.54 mm) to about 0.4 inches (10 mm). These sizes may allow the housing 22 to be implanted within different sized coronary sinuses while still allowing for sufficient blood flow through the coronary sinus 15.

The housing 22 may have one or more textures on an exterior surface thereof. In some cases, the texture(s) of the housing 22 may include a first texture that facilitates stabilization of the housing 22 at a location within the patient and a second texture that facilitates blood passing by the housing 22. In one example of when the housing 22 may be configured for placement within the coronary sinus 15 of a patient, a first side (e.g., a concave side as discussed below and/or other side) of the housing 22 intended to be adjacent to and/or touching excitable myocardial tissue may have a texturized surface (e.g., with a rough texture) to facilitate stabilizing the housing 22 at an intended location and a second side (e.g., a convex side as discussed below or other side) of the housing 22 intended to be adjacent to and/or touching fat or pericardial tissue may have a smooth surface relative to the texturized first side of the housing 22 to facilitate blood and/or other fluids passing the housing 22 within the coronary sinus 15. The texturized surface may be texturized through sandblasting, beadblasting, sodium bicarbonate-blasting, electropolishing, depositing, and/or one or more other texturizing techniques. The smooth surface may be smooth from polishing, applying a protective layer or coating, and/or one or more other smoothing techniques.

In some embodiments, the leadless pacing device 20 may additionally include one or more electrodes. In one example, the housing 22 may support a first electrode 26 and a second electrode 28, while the distal extension 24 may support a distal electrode. In some cases, the distal electrode may include a plurality of electrodes (e.g., a first proximal ring electrode 30, a second proximal ring electrode 32, a third proximal ring electrode 34, a distal ring electrode 36, and/or one or more other electrodes). Although the electrodes described may be indicated as being ring electrodes, other electrode types may be utilized depending on the application.

Although electrodes 26, 28 supported by the housing 22 are depicted as disposed on both of the first portion 22a and the second portion 22b of the housing 22, respectively, in some cases, the number and location of electrodes disposed on housing 22 may vary, depending on the application. For example, the leadless pacing device 20 may have electrodes disposed only on one of the first housing portion 22a or the second housing portion 22b, where the leadless pacing device 20 includes two housing portions. It may be desirable to arrange electrodes on the housing 22 at various longitudinal lengths of the housing 22 to facilitate creating good contact between an electrode and a wall of the coronary sinus 15. In some instances, the leadless pacing device 20 may not have any electrodes disposed on the housing 22.

In one example arrangement of the electrodes 26, 28 on the housing 22, the first electrode 26 that is located on the first portion 22a of the housing 22 may be an anode electrode and the second electrode 28 that is located on the second portion 22b of the housing 22 may be a cathode electrode. However, as the electrodes may be bipolar electrodes, the first electrode 26 in the example arrangement may be changed to a cathode electrode and the second electrode 28 in the example arrangement may be changed to an anode electrode. The polarity of paired bipolar electrodes may be switched regardless of locations of the electrodes.

When provided, the electrodes of the leadless pacing device 20 may be used to deliver electrical stimulation to heart 10, and/or sense one or more physiologic signals. In some cases, the leadless pacing device 20 may use one or more of the electrodes (e.g., electrodes 26-36 or other electrodes) to communicate with one or more other devices, such as, but not limited to, one or more other leadless cardiac pacemakers and/or an implantable cardioverter defibrillator. In some instances, the leadless pacing device 20 may communicate using conducted communication techniques and may deliver and/or receive communication signals through one or more of the electrodes (e.g., the electrodes 26-36 or other electrodes).

In some instances, the housing 22 may include a proximal member 38 (e.g., a docking hub or other member) which extends generally from the proximal end of the housing 22. In the example shown in FIG. 1, the proximal member 38 may extend from the first portion 22a of the housing 22. During implantation, the proximal member 38 may be releasably coupled to a positioning device (not shown in FIG. 1). When coupled, movement of the positioning device may translate to the housing 22, thereby allowing a user, such as a physician, to maneuver the housing 22 into a proper position within the heart 10, for example into or proximate the coronary sinus 15.

In some instances, the leadless pacing device 20 may be delivered from a guide catheter (not shown in FIG. 1), and the portion of the guide catheter surrounding the housing 22 may conform to the housing 22 to create a secure connection between the guide catheter and the housing 22. When in position, the guide catheter may be retracted, or a stylet or other pushing device may push the housing 22 out of the guide catheter. In these cases, the proximal member 38 may further include a tether anchor 40. During delivery, a tether may be coupled to the tether anchor 40 to allow a user to pull the housing 22 back within the guide catheter for further positioning. In some instances, the tether may be a string, and the string may be coupled to the tether anchor 40 by looping around the tether anchor 40. To release the tether from housing 22, a user may simply cut the tether or pull one end of the tether until the tether unloops itself from the tether anchor 40.

Although the distal extension 24 is depicted in FIG. 1, in some instances, the leadless pacing device 20 may not include the distal extension 24. Where the leadless pacing device 20 includes the distal extension 24 extending from the distal end of the housing 22 (e.g., the second portion 22b of the housing 22, as shown in FIG. 1). When included, the distal extension 24 may extend into the coronary sinus 15 and be secured within coronary sinus 15. In some cases, the distal extension 24 may extend through the coronary sinus 15 and into the great cardiac vein 17, as depicted in FIG. 1, or one or more other vessels extending from the coronary sinus.

The distal extension 24 may include a proximal end 24a and a distal end 24b. The distal end 24b of the distal extension 24 may include one or more fixing members 42. The fixing members 42 may help secure the distal end 24b of the distal extension 24 within coronary sinus 15 or great cardiac vein 17. The fixing members 42 may include one or more anchors 44 (e.g., tines, helical coils, talons, or other anchors) made of silicon, a biocompatible polymer, a biocompatible metal, another biocompatible material, a shape memory material (e.g., nitinol or other shape memory material), and/or a bioabsorbable. A bioabsorbable material may be utilized to facilitate removal of the leadless pacing device 20 from a patient as endothelial growth may otherwise occur over the anchors 44. The anchors 44 may extend radially outward from the distal extension 24 and press against the walls of great cardiac vein 17. The force between the anchors 44 and the walls of great cardiac vein 17 may hold the distal end 24b of the distal extension 24 in place.

The anchors 44 of the fixing member 42 (e.g., and thus the fixing member 42) may be angled to allow easy insertion through body vessels (e.g., veins, coronary sinus, etc.), while facilitating fixation against valves of body vessels at target sites and/or implant locations. In some cases, the anchors 44 of the fixing members 42 may be angled proximally so as to facilitate distal insertion into and/or through body vessels and may extend radially outward from a longitudinal axis of the distal extension 24 in the proximal direction to engage a valve in the body vessel and fixate the distal extension 24 at an implant location (e.g., to prevent or limit proximal movement).

Although one fixing member 42 is depicted on the distal extension 24 in the Figures, the distal extension 24 may support one or more additional fixing members that are axially spaced from the fixing member 42 depicted in the Figures. In other instances, the distal extension 24 may not include a fixing member 42.

In some cases, the fixing member 42 may include one or more electrodes or wire loops and may act as an antenna to communicate with and/or receive electrical energy from one or more other devices. For example, the leadless pacing device 20 may receive an energy transfer and/or communicate using inductive and/or conductive communication techniques through electrodes and/or wire loops of the fixing member 42.

As mentioned above, the distal extension 24 may include one or more electrodes (e.g., electrodes 30-36). In some of these instances, the electrodes 30-36 may be disposed proximate the distal end 24b of the distal extension 24 and away from the housing 22, however in other instances, one or more of the electrodes on the distal extension 24 may span a length (e.g., an entire length) of the distal extension 24.

In some cases, the electrodes on the distal extension 24 may be used to deliver electrical stimulation to the heart 10. For example, the leadless pacing device 20 may deliver electrical stimulation to the left ventricle 14 of heart 10 through a set of one or more of electrodes (e.g., a set from the electrodes 30-36 or other electrodes). In some cases, the leadless pacing device 20 may deliver electrical stimulation to the left ventricle 14 of heart 10 using two or more of the electrodes 30-36 either simultaneously or with a delay (e.g. via multi-electrode pacing). In some additional or alternative cases, the leadless pacing device 20 may use one or more of the electrodes 30-36 to communicate with one or more other devices (e.g., the electrodes 30-36 may act as an antenna). For example, the leadless pacing device 20 may receive an energy transfer and/or communicate using inductive or conductive communication techniques through one or more of the electrodes 30-36.

The electrodes 26-36 and/or other electrodes on the leadless pacing device 20 may be able to sense electrical signals, provide electrical stimulation signals, or sense electrical signals and provide electrical stimulation signals. Signal processing, communication, and/or therapy pulse generation may take place at any portion of the leadless pacing device where the appropriate processing modules may be located. In one example, signal processing, communication, and therapy pulse generation for the electrodes (e.g., electrodes 26-36 and/or other electrodes) of the leadless pacing device 20 may take place in modules within or supported by the housing 22, but this is not required.

The electrodes 26-36 and/or other electrodes of the leadless pacing device 20 may be configured to perform near-field and/or far-field sensing of cardiac activation events. "Near-field" sensing of cardiac activation events refers to sensing cardiac activation events that originate in a local chamber where the corresponding electrode is located (e.g., the same chamber at which an electrode is sensing). "Far-field" sensing of cardiac activation events refers to sensing cardiac activation events that originate in a chamber other than the local chamber where the corresponding electrode is located. For example, if an electrode of the leadless pacing device 20 is located in the coronary sinus 15 with an electrode adjacent a wall of the coronary sinus 15 that forms a wall of the right atrium 11, the electrode is near-field sensing right atrium activation events and is far-field sensing left atrium activation events, left, ventricle activation events, and right ventricle activation events.

In the example of FIG. 1 where the leadless pacing device 20 is implanted in the coronary sinus 15 and a vessel (e.g., the great cardiac vein 17) extending from the coronary sinus 15, the first electrode 26 (e.g., a proximally located electrode on the housing 22) may be located in the coronary sinus 15 adjacent the right atrium 11, the second electrode 28 (e.g., a distally located electrode on the housing 22) may be located in the coronary sinus 15 adjacent the left atrium 12, and the electrodes 30-36 supported by the distal extension 24 may be located in the great cardiac vein 17 adjacent the left ventricle 14. In such an implanted configuration, the first electrode 26 may sense near-field signals of atrial activation events (P-waves) in and provide pacing pulses to cardiac tissue of the right atrium 11, the second electrode may sense near-field signals of atrial activation events (P-waves) in and provide pacing pulses to cardiac tissue of the left atrium 12, and the electrodes 30-36 supported by the distal extension 24 may sense near-field signals of ventricular activation events (R-waves) originating from atria and conducted through the atrioventricular node and His-Purkinje path in and provide pacing pulses to cardiac tissue of the left ventricle 14.

Additionally or alternatively, the electrodes 26-36 or other electrodes of the leadless pacing device 20 may sense signals through far-field sensing. For example, the electrodes 26, 28 that may be supported by the housing 22 may sense far-field ventricular activation activity (R-waves) and the electrodes 30-36 supported by the distal extension 24 may sense far-field atrial activation activity (P-waves). However, such sensed signals may be attenuated and delayed and/or the amplitude and duration may be insufficient for reliable sensing of atrial and ventricular activation activity and it may be necessary to consider signals sensed through near-field sensing when considering signals sensed through far-field sensing.

In some cases, the leadless pacing device 20 may be implanted as a single device (e.g. without one or more other leadless pacing devices or one or more implantable cardioverter defibrillators), which may provide electrical stimulation to the right atrium 11, the left atrium 12, right ventricle 13 and/or the left ventricle 14, as desired. For example, the leadless pacing device 20 may be configured to deliver electrical stimulation in accordance with a therapy program to treat atrial fibrillation or atrial flutter. However, in other cases, the leadless pacing device 20 may be implanted with one or more other leadless pacing devices and/or one or more other implantable cardioverter defibrillators implanted at one or more various locations in and/or around the heart 10.

In one example of using the leadless pacing device 20, the leadless pacing device 20 may be part of a single or multiple device system for delivering cardiac resynchronization therapy (CRT) to heart 10. In these examples, the leadless pacing device 20 may sense cardiac electrical signals in one or both of right atrium 11 and left atrium 12. Once the leadless pacing device 20 senses cardiac electrical signals propagating through the right atrium 11 and/or left atrium 12, the leadless pacing device 20 may deliver a pacing pulse to the left ventricle 14 after a delay period (e.g. an AV delay). The length of the delay period may be determined or chosen such that the leadless pacing device 20 may deliver a pacing pulse to the left ventricle 14 as the propagating cardiac electrical signals reach the right ventricle 13 and cause the right ventricle 13 to contract. In this manner, the leadless pacing device 20 may operate to provide synchronous contractions of the right ventricle 13 and the left ventricle 14. In some additional instances, the leadless pacing device 20 may adjust the delay period based on a sensed heart rate. For example, when the leadless pacing device 20 senses an increased heart rate, the leadless pacing device 20 may shorten the length of the delay period. Conversely, when the leadless pacing device 20 senses a lowered heart rate, the leadless pacing device 20 may lengthen the delay period.

As discussed, the leadless pacing device 20 may deliver pacing pulses to the right atrium 11 and/or the left atrium 12 via the coronary sinus 15. In these embodiments, the leadless pacing device 20 may begin counting the delay period at the time of or just after the leadless pacing device 20 delivers a pacing pulse to the right atrium 11 and/or the left atrium 12. As with the previously described embodiments, this may cause synchronous contractions of the right ventricle 13 and the left ventricle 14. Where the leadless pacing device 20 is part of a system with an additional leadless pacing device within the right ventricle 13, the leadless pacing device 20 may communicate a trigger to the additional leadless pacing device after the leadless pacing device 20 delivers a pacing pulse to the right atrium 11 and/or the left atrium 12. After receiving the trigger, the additional leadless pacing device may deliver a pacing pulse to the right ventricle 13 after its own delay period. In at least some of the examples, the delay period of the additional leadless pacing device and the delay period of the leadless pacing device 20 may be in alignment such that both of the additional leadless pacing device and the leadless pacing device 20 deliver pacing pulses to the right ventricle 13 and the left ventricle 14 synchronously. However, in other embodiments, the delay period of the additional leadless pacing device and the delay period of the leadless pacing device 20 may be different, for instance if conduction through the right ventricle 13 and left ventricle 14 differ, in order to cause right ventricle 13 and left ventricle 14 to contract synchronously.

Figure 2:
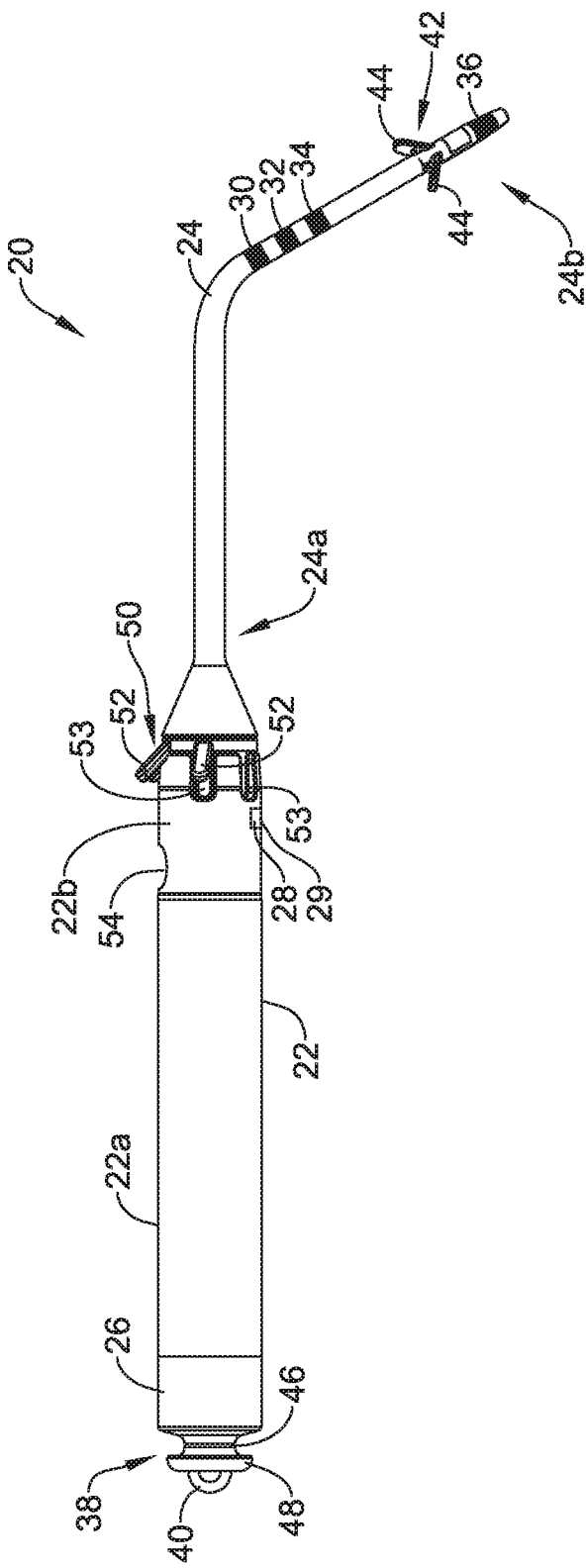
FIG. 2 is a side view of an example implantable leadless pacing device.

FIG. 2 is a schematic diagram of an illustrative the leadless pacing device 20. The illustrative leadless pacing device 20 may include the housing 22 having a first housing portion 22*a* and a second housing portion 22*b*, sometimes with the distal extension 24 extending distally of the housing 22. The housing 22 may be a unitary housing or may include two or more housing portions (e.g., the first portion 22*a*, the second portion 22*b*, and/or one or more other housing portions) in which one or more components of the leadless pacing device 20 are housed. The housing 22 may generally include a biocompatible material, such as a biocompatible metal and/or polymer, and, when implanted within a patient's body, may hermetically seal the components of the leadless pacing device 20 from fluids and tissues of the patient's body. The leadless pacing device 20 may additionally have one or more electrodes, such as electrodes 26, 28 and/or other electrodes, which in the example shown, are supported by the housing 22 (e.g., reside on the housing 22, extend from the housing 22, and/or are otherwise supported in some manner by the housing 22). It is contemplated in some cases that the housing 22 may have a different number of electrodes, or no electrodes at all.

In instances when the housing 22 includes two or more portions, the first portion 22*a* may be a body and the second portion 22*b* may be a header. The first portion 22*a* (e.g., the body) may be made from a biocompatible metal material or other material suitable for enclosing electronic components of the leadless pacing device 20. The second portion 22*b* (e.g., the header) may be made from a biocompatible polymer or other material. In some instances, the second portion may be made from a polymer and molded over a distal end of the first portion 22*a* of the housing 22 with an over molding process. When the second portion 22*b* is formed from a molding technique, the distal extension 24 may be connected to the housing 22 by molding the second portion 22*b* over the proximal end of the distal extension 24.

In some instances and as discussed above, the housing 22 may include the proximal member 38 (e.g., the docking hub) extending from a proximal end of the first portion 22*a* of the housing 22. In some cases, the proximal member 38 may have an extension 46 having a first outer diameter and projecting from the housing 22, where a proximal end of the extension 46 may be connected to or form an appendage 48 having a second diameter. In the example shown in FIG. 2, the second outer diameter of the appendage 48 may be greater than the first outer diameter of the extension 46, but other suitable configurations are contemplated.

During implantation, a positioning device may releasably couple to the proximal member 38. When coupled, movement of the positioning device may translate to the housing 22, thereby allowing a user to position the leadless pacing device 20 during implantation. In some cases, instead of or in addition to the extension 46 and the appendage 48, the proximal member 38 may include one-half of an interlocking mechanism, and the positioning device may have the second half of the interlocking mechanism, which may releasably couple to the interlocking mechanism of proximal member 38.

In some instances, the housing 22 may include a fixing member 50. The fixing member may be configured to maintain the leadless pacing device 20 within the coronary sinus 15 when the leadless pacing device 20 is implanted within the coronary sinus 15 of the heart 10. The fixing member 50 may include one or more anchors 52 (e.g., tines, helical coils, talons, or other anchors) made of silicon, a biocompatible polymer, a biocompatible metal, another biocompatible material, a shape memory material (e.g., nitinol or other shape memory material) and/or a bioabsorbable. A bioabsorbable material may be utilized to facilitate removal of the leadless pacing device 20 from a patient as growth may otherwise occur over the anchors 52. The anchors 52 may extend radially outward from the distal extension 24 and press against the walls of the coronary sinus 15. The force between the anchors 52 and the walls of coronary sinus 15 may hold the housing 22 in place within the coronary sinus 15.

The anchors 52 of the fixing member 50 (e.g., and thus the fixing member 50) may be angled to allow easy insertion through body vessels (e.g., veins, coronary sinus, etc.), while facilitating fixation against valves of body vessels at target sites and/or implant locations. In some cases, the anchors 52 of the fixing members 50 may be angled proximally so as to facilitate distal insertion into and/or through body vessels and may extend radially outward from a longitudinal axis of the housing 22 in the proximal direction to engage a valve in the body vessel and fixate the housing 22 at an implant location (e.g., to prevent or limit proximal movement).

In at least some examples, the fixing member 50 may further maintain the housing 22 in a desired disposition with respect to the lumen of coronary sinus 15, for instance floating in the middle of the lumen of the coronary sinus 15 (e.g., when the anchors 52 are equally, circumferentially spaced around the housing 22) or pressed up against the wall of coronary sinus 15 that forms a wall of a chamber of the heart 10 (e.g., when the anchors 52 are circumferentially spaced, but not equally so, around the housing 22).

Although one fixing member 50 is depicted on the housing 22 in the Figures, the housing 22 may support one or more additional fixing members that are axially spaced from the fixing member 50 depicted in the Figures. In other instances, the housing 22 may not include a fixing member 50.

In some cases, the fixing member 50 (and/or fixing member 42) may include one or more electrodes or wire loops and may act as an antenna to communicate with and/or receive electrical energy from one or more other devices. For example, the leadless pacing device 20 may receive an energy transfer and/or communicate using inductive and/or conductive communication techniques through electrodes and/or wire loops of the fixing member 50.

The second portion 22*b* of the housing 22 may include one or more recesses 53. In one example, the second portion 22*b* of the housing 22 may include a recess 53 aligned with each anchor 52 of the fixing member 50 such that the anchors 52 may articulate in response to an applied force (e.g., from a guide catheter, introducer sheath, etc.) and be positioned at least partially within a corresponding recess 53 during delivery of the leadless pacing device to a target location (e.g., the coronary sinus 15).

In at least some cases, the housing 22 may have guide wire port 54 extending through a side of the housing 22, where the side extends from a first end to a second of the housing 22. In some cases, the guide wire port 54 may be disposed in or proximate the second portion 22*b* of the housing 22 and may be configured to receive a guide wire. Where the leadless pacing device 20 includes the distal extension 24, the distal extension 24 may include a corresponding guide wire port extending out of a distal tip of the distal end 24b of the distal extension 24. In such instances, a guide wire may be placed down the great cardiac vein 17 (or other vessel in communication with the coronary sinus 15). The leadless pacing device 20 may be tracked over the guide wire by threading the distal extension 24 over a proximal end of the guide wire, and then advancing the leadless pacing device 20 over the guide wire until in position. In embodiments where the leadless pacing device 20 does not include the distal extension 24, the housing 22 may include a second guide wire port.

The distal extension 24 may be a thin, elongated, and flexible member, particularly in relation to the housing 22. For instance, the distal extension 24 may be between two and ten times the length of the housing 22. Additionally and as discussed above, the distal extension 24 may have one or more fixing members 42. In some cases, the fixing member 42 may be disposed at or near the distal end 24b of the distal extension 24. In some cases, the distal extension 24 may include one or more electrodes (e.g., electrodes 30-36).

The electrodes 30-36 and/or other electrodes may be disposed proximate the distal end 24b of the distal extension 24, or may be spread out along the length of distal extension 24 (e.g., longitudinally spaced from one another), as shown in FIG. 2. Other arrangements and/or configurations of electrodes on the distal extension 24 are contemplated and may be utilized. In one example arrangement of electrodes (e.g., utilizing electrodes 30-36), each of the electrodes may be ring electrodes and the electrode 36 (e.g., a distal ring electrode) may be the disposed on the distal extension 24 near a distal tip of the distal extension 24, the electrode 34 (e.g., a third proximal ring electrode) may be spaced forty (40) millimeters proximal of the electrode 36, the electrode 32 (e.g., a second proximal ring electrode) may be spaced ten (10) millimeters proximal of the electrode 34, and the electrode 30 (e.g., a first proximal ring electrode) may be spaced ten (10) millimeters proximal of the electrode 32. Such a configuration of electrodes 30-36 may align with the left atrium 12 when the distal extension 24 is inserted into the great cardiac vein 17 or other vessel to allow the leadless pacing device 20 to sense and/or pace the left atrium 12 of the patient's heart 10. In some cases, the distal extension 24 may be biased to form a shape such as a helical coil or one or more loops.

Figure 3:
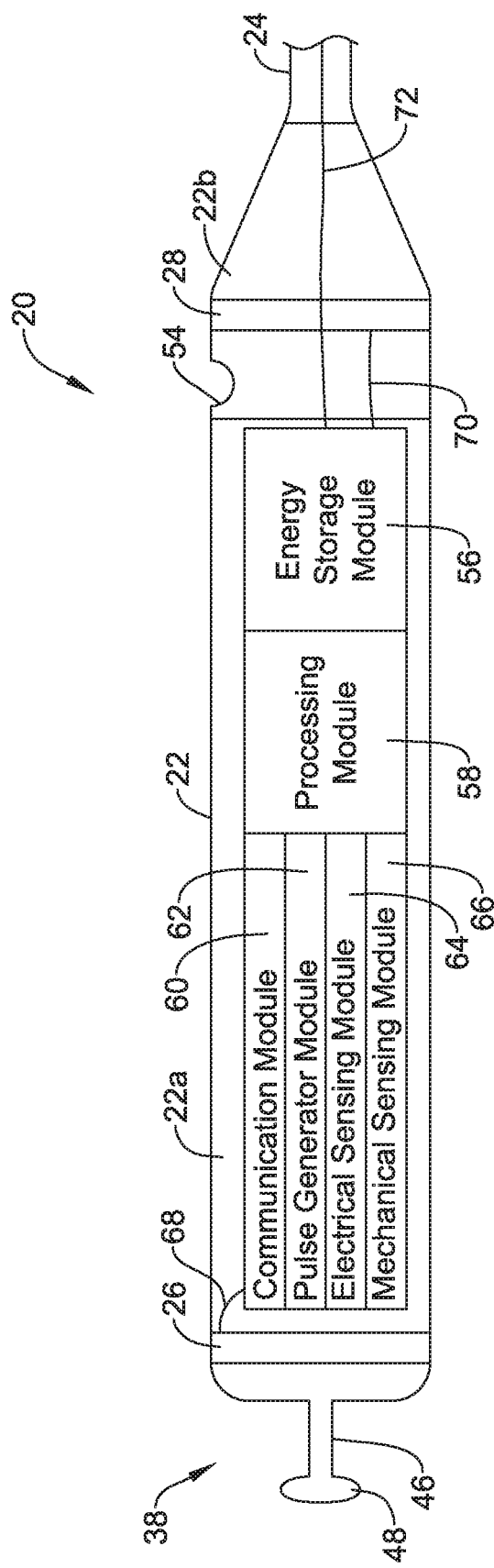
FIG. 3 is a schematic block diagram of an example implantable leadless pacing device.

FIG. 3 is a schematic block diagram of one or more electronics modules that may be contained within the housing 22 of the leadless pacing device 20. In some instances, the leadless pacing device 20 may include an energy storage module 56 (e.g., a power supply for supplying/providing a power supply voltage), a processing module 58, a communication module 60, a pulse generator module 62, an electrical sensing module 64, and/or a mechanical sensing module 66. FIG. 3 also depicts conductors 68-72 that may extend from one or more of modules 56, 58, 60, 62, 64, and/or to one or more electrodes (e.g., the electrodes 26-36 or other electrodes). Although only three conductors are depicted in FIG. 3, a different conductor may extend from the modules in the housing 22 to each of the electrodes of the leadless pacing device 20. Accordingly, in at least some instances, all of the electronic elements and energy storage modules of the leadless pacing device 20 may be contained within the housing 22, while only the one or more conductors extend to the electrodes. In one example, the conductor 68 may extend to the first electrode 26 supported by the housing 22, the conductor 70 may extend to the second electrode 28 supported by the housing 22, and the conductor 72 may be representative of the conductors extending to the electrodes 30-36 on the distal extension, where a single conductor may extend to each electrode 30-36 and the conductor extending to the distal ring electrode 36 may be coiled along and/or around a lumen 76 of the distal extension 24 until the conductor reaches the distal ring electrode 36. Additionally or alternatively, other conductors may be coiled around the lumen 76, as desired. Each conductor extending to an electrode may be electrically isolated from the other conductors and in some cases, each conductor may extend to an associated electrode through its own lumen, but this is not required.

In the example shown FIG. 3, the communication module 60 may be electrically coupled to electrodes 26-36 and may be configured to deliver communication signals, such as electrical communication pulses, to tissues of the patient for communicating with other devices such as sensors, programmers, other medical devices, and/or the like. Electrical communication pulses, as used herein, may be any modulated signal that conveys information to another device, either by itself or in conjunction with one or more other modulated signals. In some embodiments, electrical communication pulses may be limited to sub-threshold signals that do not result in capture of the heart yet still convey information. The electrical communication pulses may be delivered to another device that is located either external or internal to the patient's body. The communication module 60 may additionally be configured to sense for electrical communication pulses delivered by other devices, which may be located external or internal to the patient's body.

The communication module 60 may communicate to help accomplish one or more desired functions. Some example functions include delivering sensed data, using communicated data for determining occurrences of events such as arrhythmias, coordinating delivery of electrical stimulation therapy, and/or other functions. In some cases, leadless pacing device 20 may use electrical communication pulses to communicate raw information, processed information, messages and/or commands, and/or other data. Raw information may include information such as sensed electrical signals (e.g. a sensed ECG), signals gathered from coupled sensors, and the like. In some embodiments, the processed information may include signals that have been filtered using one or more signal processing techniques. Processed information may also include parameters and/or events that are determined by the leadless pacing device 20 and/or another device, such as a determined heart rate, timing of determined heartbeats, timing of other determined events, determinations of threshold crossings, expirations of monitored time periods, activity level parameters, blood-oxygen parameters, blood pressure parameters, heart sound parameters, and the like. Messages and/or commands may include instructions or the like directing another device to take action, notifications of imminent actions of the sending device, requests for reading from the receiving device, requests for writing data to the receiving device, information messages, and/or other messages commands.

The pulse generator module 62 may be configured to generate electrical stimulation pulses and deliver the electrical stimulation pulses to tissues of a patient via one or more of the electrodes 26-36 in order to effectuate one or more electrical stimulation therapies. Electrical stimulation pulses as used herein are meant to encompass any electrical signals that may be delivered to tissue of a patient for purposes of treatment of any type of disease or abnormality. For example, when used to treat heart disease, the pulse generator module 62 may generate electrical stimulation pacing pulses for capturing the heart of the patient, i.e. causing the heart to contract in response to the delivered electrical stimulation pulse. In another embodiment, the electrical stimulation pulses may be defibrillation/cardioversion pulses for shocking the heart out of fibrillation. In yet another embodiment, the electrical stimulation pulses may be anti-tachycardia pacing (ATP) pulses. These are just some examples. When used to treat other ailments, the pulse generator module 62 may generate electrical stimulation pulses suitable for neurostimulation therapy or the like. The pulse generator module 62 may include one or more capacitor elements and/or other charge storage devices to aid in generating and delivering appropriate electrical stimulation pulses. In the embodiment shown, the pulse generator module 62 may use energy stored in the energy storage module 56 to generate the electrical stimulation pulses.

In at least some embodiments, the communication module 60 (or otherwise the leadless pacing device 20) may further include switching circuitry to selectively connect one or more of electrodes 26-36 to the communication module 60 in order to select to which electrodes 26-36 that the communication module 60 delivers electrical communication pulses. It is contemplated that the communication module 60 may communicate with other devices via conducted signals, radio frequency (RF) signals, optical signals, acoustic signals, inductive coupling, and/or any other suitable communication methodology.

The pulse generator module 62 may include the capability to modify the electrical stimulation pulses, such as by adjusting the pulse width and/or amplitude of the electrical stimulation pulses. When pacing the heart, this may help tailor the electrical stimulation pulses to capture the heart of a particular patient, sometimes with reduced battery usage. For neurostimulation therapy, adjusting the pulse width and/or amplitude may help tailor the therapy for a particular application and/or help make the therapy more effective for a particular patient.

The electrical sensing module 64 may be electrically connected to one or more electrodes 26-36 and the electrical sensing module 64 may be configured to receive cardiac electrical signals conducted through electrodes 26-36. In some embodiments, the cardiac electrical signals may represent local information (e.g., near-field information) from the chamber at or about which an electrode of the leadless pacing device 20 is located when the leadless pacing device 20 has been implanted in the coronary sinus 15 and/or a vessel extending therefrom. For instance, if an electrode(s) of the leadless pacing device 20 is located at or about a ventricle of the heart, the cardiac electrical signals sensed by the electrode(s) may be near-field signals and may represent ventricular cardiac electrical signals.

The mechanical sensing module 66 may include, or be electrically connected to, various sensors, such as accelerometers, blood pressure sensors, heart sound sensors, blood-oxygen sensors, and/or other sensors which measure one or more physiological parameters of the heart and/or patient. The mechanical sensing module 66, when present, may gather signals from the sensors indicative of the various physiological parameters. Both the electrical sensing module 64 and the mechanical sensing module 66 may be connected to the processing module 58 and may provide signals representative of the sensed cardiac electrical signals and/or physiological signals to the processing module 58. Although described with respect to FIG. 2 as separate sensing modules, in some embodiments, the electrical sensing module 64 and the mechanical sensing module 66 may be combined into a single module.

The processing module 58 may be configured to control the operation of the leadless pacing device 20. For example, the processing module 58 may be configured to receive near-field and/or far-field cardiac electrical signals from the electrical sensing module 64 and/or physiological signals from the mechanical sensing module 66. Based on the received near-field and/or far-field signals, the processing module 58 may determine, for example, occurrences and types of arrhythmias (e.g., when an atrial and/or a ventricular event occurs). In one example, the processing module 58 may identify P-waves, R-waves, T-waves, and/or other cardiac events of interest, along with the relative timing of each wave/event.

In one example of an implanted leadless pacing device 20 as seen in FIG. 1, the processing module 58 may determine whether an atrial event occurred based on near-field signals sensed using one or more of the electrodes 26, 28 supported by the housing 22, determine whether a ventricular event occurred based on near-field signals sensed using one or more of electrodes 30-36 supported by the distal extension 24, and/or determine whether an atrial event or ventricular event occurred based on near-field signals sensed using spatially opposed electrodes in a bipolar or other configuration (e.g., one or more of the electrodes 26, 28 on the housing 22 and one or more of the electrodes 30-36 on the distal extension 24). Additionally, or alternatively, the processing module 58 may determine whether a ventricular event occurred based on far-field signals sensed using one or more of electrodes 26, 28, determine whether an atrial event occurred based on far-field signals sensed using one or more of electrodes 30-36, and/or determine whether an atrial event or ventricular event occurred based on far-field signals sensed using spatially opposed electrodes in a bipolar or other configuration (e.g., one or more of the electrodes 26, 28 on the housing 22 and one or more of the electrodes 30-36 on the distal extension 24). Further, depending on which electrode(s) sensed a signal, the processing module 58 may determine at which chamber a determined cardiac activation event occurred based on one or more of a type of sensed signal (e.g., far-field or near-field), a location within the heart 10 of an electrode sensing the signal, and a timing of the sensed signal relative to one or more other sensed signals. For example, the processing module may indicate that a determined cardiac event based on a near-field signal sensed from the first electrode 26 at the right atrium 11 indicates the cardiac event is a right atrial cardiac activation event.

The processing module 58 may further receive information from the communication module 60. In some embodiments, the processing module 58 may additionally use such received information to determine occurrences and types of arrhythmias. However, in other embodiments, the leadless pacing device 20 may use the received information instead of the signals received from the electrical sensing module 64 and/or the mechanical sensing module 66. For instance, if the received information is more accurate than the signals received from the electrical sensing module 64 and/or the mechanical sensing module 66 or if the electrical sensing module 64 and/or the mechanical sensing module 66 have been disabled or omitted from the leadless pacing device 20.

Based on a determined arrhythmia (e.g., a determined atrial and/or ventricular cardiac event), the processing module 58 may control the pulse generator module 62 to generate electrical stimulation pulses in accordance with one or more electrical stimulation therapies to treat the determined arrhythmia. For example, the processing module 58 may control the pulse generator module 62 to generate pacing pulses with varying parameters and in different sequences to effectuate one or more electrical stimulation therapies. For example, in controlling the pulse generator module 62 to deliver bradycardia pacing therapy, the processing module 58 may control the pulse generator module 62 to deliver pacing pulses designed to capture the heart of the patient at a regular interval to help prevent the heart of a patient from falling below a predetermined threshold. In some cases, the rate of pacing may be increased with an increased activity level of the patient (e.g. rate adaptive pacing). For ATP therapy, the processing module 58 may control the pulse generator module 62 to deliver pacing pulses at a rate faster than an intrinsic heart rate of a patient in an attempt to force the heart to beat in response to the delivered pacing pulses rather than in response to intrinsic cardiac electrical signals. Once the heart is following the pacing pulses, the processing module 58 may control the pulse generator module 62 to reduce the rate of delivered pacing pulses down to a safer level. In CRT, the processing module 58 may control the pulse generator module 62 to deliver pacing pulses in coordination with another device to cause the heart to contract more efficiently. In cases where the pulse generator module 62 is capable of generating defibrillation and/or cardioversion pulses for defibrillation/cardioversion therapy, the processing module 58 may control the pulse generator module 62 to generate such defibrillation and/or cardioversion pulses. In some cases, the processing module 58 may control the pulse generator module 62 to generate electrical stimulation pulses to provide electrical stimulation therapies different than those examples described above.

Aside from controlling the pulse generator module 62 to generate different types of electrical stimulation pulses and in different sequences, in some embodiments, the processing module 58 may also control the pulse generator module 62 to generate the various electrical stimulation pulses with varying pulse parameters. For example, each electrical stimulation pulse may have a pulse width and a pulse amplitude, and may be directed from one or more electrodes. The processing module 58 may control the pulse generator module 62 to generate the various electrical stimulation pulses with specific pulse widths, specific pulse amplitudes, and specific electrodes (e.g., one or more of electrodes 26-36 or other electrodes of the leadless pacing device 20). As one example, the processing module 58 may cause the pulse generator module 62 to adjust the pulse width and/or the pulse amplitude of electrical stimulation pulses if the electrical stimulation pulses are not effectively capturing the heart. Such control of the specific parameters of the various electrical stimulation pulses may help the leadless pacing device 20 provide more effective delivery of electrical stimulation therapy.

In some embodiments, the processing module 58 may further control the communication module 60 to send information to other devices. For example, the processing module 58 may control the communication module 60 to generate one or more electrical communication pulses for communicating with other devices of a system of devices. For instance, the processing module 58 may control the communication module 60 to generate electrical communication pulses in particular sequences, where the specific sequences convey different information. The communication module 60 may also receive communication signals for potential action by the processing module 58.

In further instances, the processing module 58 may control switching circuitry by which the communication module 60 and the pulse generator module 62 deliver electrical communication pulses and/or electrical stimulation pulses to tissue of the patient. As described above, both of the communication module 60 and the pulse generator module 62 may include circuitry for connecting one or more electrodes 26-36 to the communication module 60 and/or the pulse generator module 62 so those modules may deliver the electrical communication pulses and electrical stimulation pulses to tissue of the patient via one or more of the electrodes 26, 28 supported by the housing 22 and/or one or more of the electrodes 30, 32, 34, 36 supported by the distal extension 24. The specific combination of one or more electrodes by which the communication module 60 and/or the pulse generator module 62 deliver electrical communication pulses and electrical stimulation pulses may influence the reception of communication pulses and/or the effectiveness of electrical stimulation pulses. Although it was described that each of the communication module 60 and the pulse generator module 62 may include switching circuitry, in some embodiments, the leadless pacing device 20 may have a single switching module connected to the communication module 60, the pulse generator module 62, and electrodes 26-36 of the leadless pacing device 20. In such cases, the processing module 58 may control the switching module to connect modules 60/62 and electrodes 26-36 of the leadless pacing device 20 as appropriate to generate electrical communication pulses and electrical stimulation pulses to the tissue of the patient via one or more of the electrodes 26, 28 supported by the housing 22 and/or one or more of the electrodes 30, 32, 34, 36 supported by the distal extension 24.

In some instances, the processing module 58 may include a pre-programmed chip, such as a very-large-scale integration (VLSI) chip or an application specific integrated circuit (ASIC). In such embodiments, the chip may be pre-programmed with control logic in order to control the operation of the leadless pacing device 20. By using a pre-programmed chip, the processing module 58 may use less power than other programmable circuits while able to maintain basic functionality, thereby potentially increasing the battery life of the leadless pacing device 20. In other instances, the processing module 58 may include a programmable microprocessor or the like. Such a programmable microprocessor may allow a user to adjust the control logic of the leadless pacing device 20 after manufacture, thereby allowing for greater flexibility of the leadless pacing device 20 than when using a pre-programmed chip.

The processing module 58, in additional instances, may include a memory circuit and the processing module 58 may store information on and read information from the memory circuit. In other instances, the leadless pacing device 20 may include a separate memory circuit (not shown) that is in communication with the processing module 58, such that the processing module 58 may read and write information to and from the separate memory circuit. The memory circuit, whether part of the processing module 58 or separate from the processing module 58, may be volatile memory, non-volatile memory, or a combination of volatile memory and non-volatile memory.

The energy storage module 56 may provide a power source to the leadless pacing device 20 for its operations. In some embodiments, the energy storage module 56 may be a non-rechargeable lithium-based battery. In other embodiments, the non-rechargeable battery may be made from other suitable materials. In some embodiments, the energy storage module 56 may include a rechargeable battery. In still other embodiments, the energy storage module 56 may include other types of energy storage devices such as super capacitors.

Figure 4:
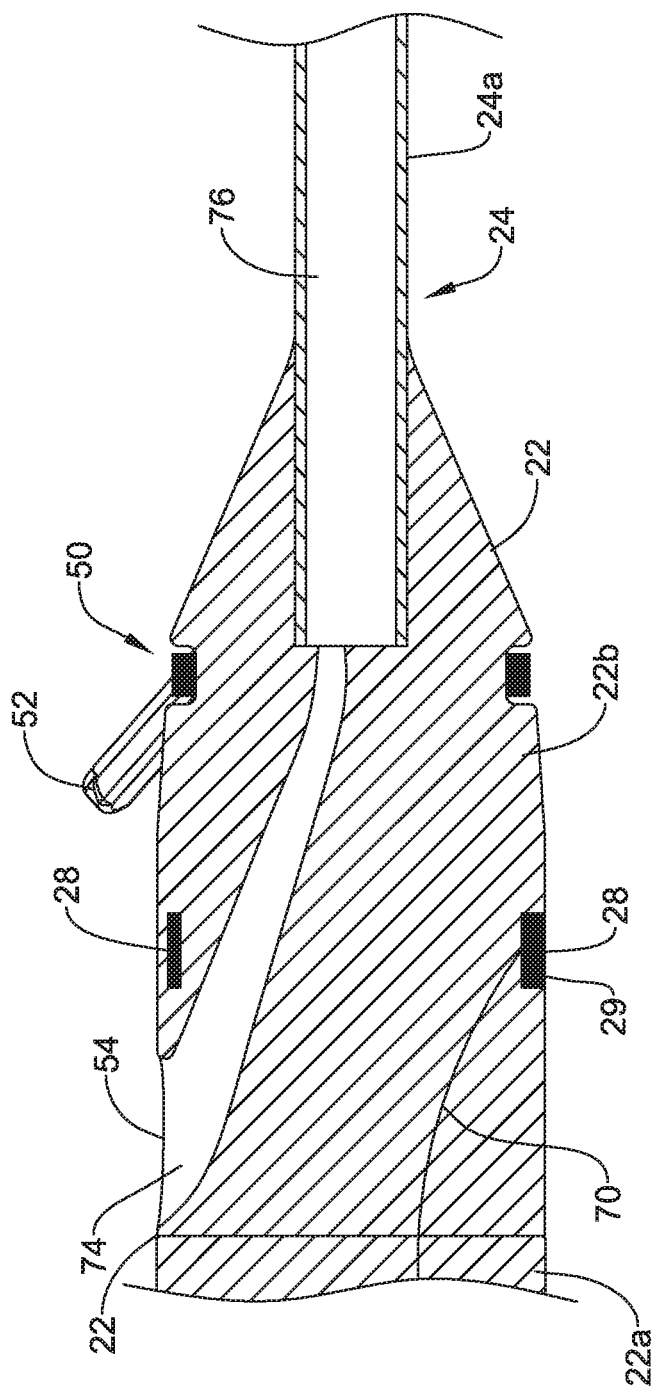
FIG. 4 is a cross-sectional side view of a distal portion of an example implantable leadless pacing device.

FIG. 4 depicts a partial schematic cross-sectional view of the second portion 22*b* of the housing 22 and the proximal portion 24*a* of the distal extension 24. As seen in FIG. 4, the guide wire port 54 in a side of the second portion 22*b* of the housing 22 is at a proximal end of a guide wire lumen 74 formed through the second portion 22*b* of the housing 22. The guide wire lumen 74 may extend through the second portion 22*b* of the housing 22 to a proximal end of a lumen 76 of the distal extension 24, where the lumen 76 ends at a distal port (not shown in FIG. 4). The guide wire port 54, the guide wire lumen 74, and the lumen ix) 76 extending through the distal extension 24 may form a passage for receiving a guide wire to facilitate the leadless pacing device 20 tracking a guide wire to a target location. In some cases, the leadless pacing device 20 may track over a guide wire using a rapid exchange technique, where a wire is back-loaded through a distal port in the distal extension 24 that is in communication with the lumen 76 and threaded through the lumen 76, the guide wire lumen 74, and the guide wire port 54. Other guide wire tracking techniques may be utilized.

The guide wire lumen 74 extending through the second portion 22*b* of the housing may be formed in any manner. In one example and when the second portion 22*b* may be formed by an over molding process, a core material may be inserted into the over mold, the molding material (e.g., urethane resin, silicon, and/or other biocompatible molding material suitable for over molding processes) may be applied, and the core material may be removed from the over mold material to form the guide wire port 54 and the guide wire lumen 74 once the over mold material sets. Such positioning of the guide wire port 54 in the second portion 22*b* of the housing 22 may facilitate hermetically sealing the components of the first portion 22*a* of the housing 22 within the first portion 22*a*.

The guide wire port 54 may be formed along any portion of the housing 22. As shown in FIG. 4, the guide wire port 54 may be located between a proximal end of the second portion 22*b* of the housing 22 and the second electrode 28 positioned within the second portion 22*b* of the housing 22. In some cases, the guide wire port 54 may be formed at an opposite side of the housing 22 from an exposed portion 29 of the second electrode 28, as shown in FIG. 4. The exposed portion 29 of the second electrode 28 may be an entire portion of an electrode or may be a portion of an electrode that is exposed through material of the second portion 22*b* of the housing 22 while another portion the electrode may be covered by the material of the second portion 22*b*. In one example, the second electrode 28 may be a ring electrode and one or more portions of the second electrode 28 may be exposed through the material of the housing to form exposed portion(s) 29 of the second electrode 28.

Such a configuration of the guide wire port 54 and the exposed portion 29 of the second electrode 28 relative to one another may facilitate contact between the exposed portion 29 of the second electrode 28 and a target location within a patient's body. For example, a guidewire will want to follow a largest radius of curvature as possible and as the coronary sinus 15 of a patient extends around the heart 10, a guidewire inserted into the coronary sinus may naturally track along an outside wall of the coronary sinus (e.g., a wall opposite a wall of the coronary sinus forming a wall of a chamber of the heart 10) due to the guidewire being able to follow a radius of curvature larger than it would otherwise be able to follow.

Thus, in the example, when the guide wire port 54 is located on an opposite side of the second portion 22*b* of the housing 22 from the exposed portion 29 of the electrode 28, the guide wire port 54 may be adjacent a wall of the coronary sinus 15 spaced from the wall of the coronary sinus 15 that forms a chamber of the heart 10 and as a result, the exposed portion 29 of the electrode 28 may be positioned adjacent the wall of the coronary sinus 15 that forms a wall of a chamber of the heart 10.

Figure 5:
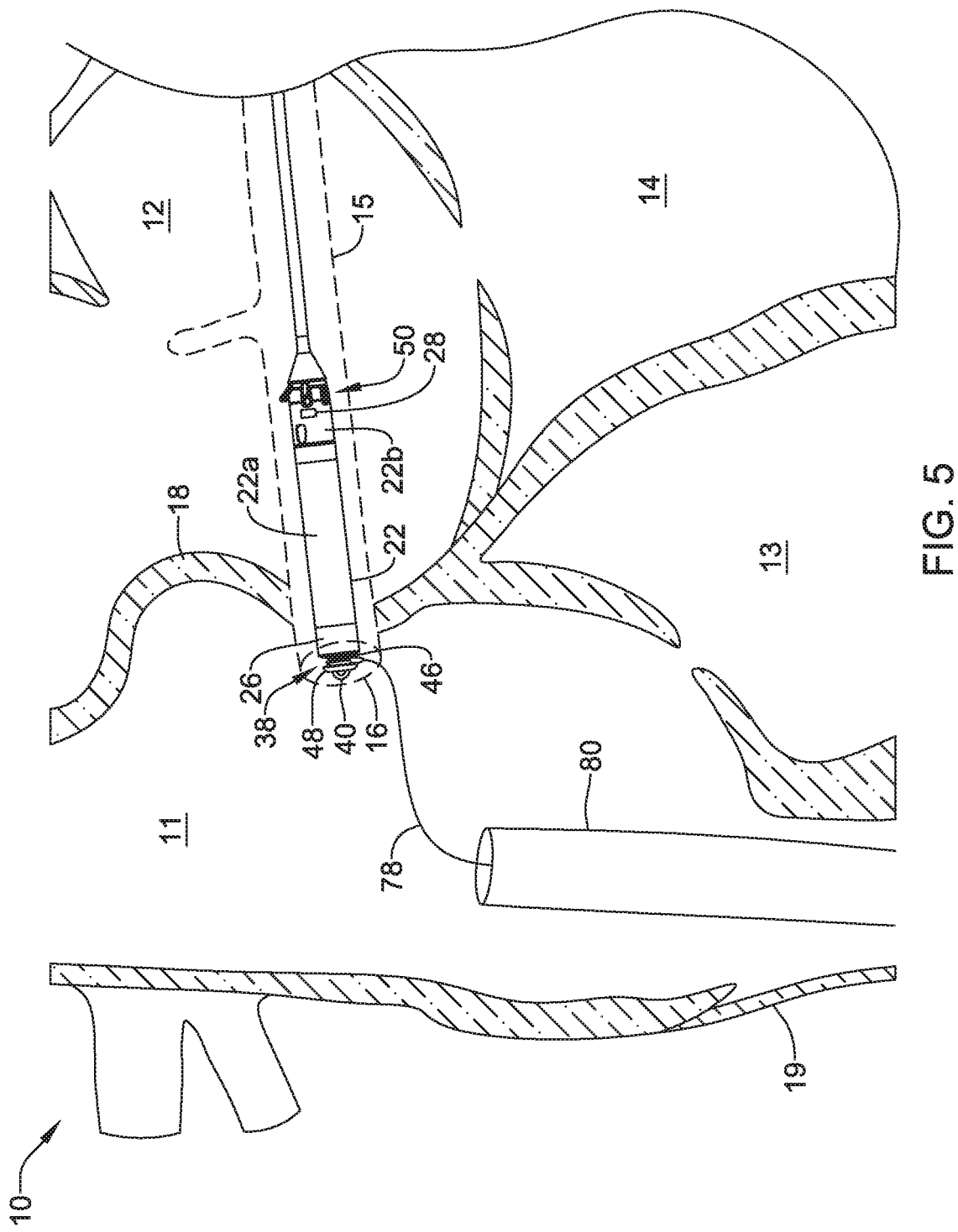
FIG. 5 is a schematic diagram of an example retrieval device for use with an example implantable leadless pacing device in a heart.

FIG. 5 depicts a close-up of the leadless pacing device 20 implanted within the heart 10 of FIG. 1. The leadless pacing device 20 may be configured such that the majority or the entirety (as shown in FIG. 5) of the housing 22 is disposed within coronary sinus 15. In some cases, the housing 22 may have the proximal member 38 extending proximally from the housing 22, and the leadless pacing device 20 may be configured such that when the leadless pacing device 20 is implanted, the proximal member 38 may extend proximally through the coronary sinus ostium 16 and into the right atrium 11. In the example of FIG. 5, where the proximal member 38 extends through coronary sinus ostium 16 to the right atrium 11, the proximal member 38 may be easier to access than if disposed in other locations (e.g., within the coronary sinus 15 or other location), thereby allowing for easier retrieval of the leadless pacing device 20 by a retrieval device 78 (e.g., a snare or other device having an elongated body for extending through vasculature and an engaging distal end configured to engage the proximal member 38 of the leadless pacing device 20) extending through a catheter 80 (e.g., a guide catheter or delivery catheter) inserted into the right atrium 11, should the leadless pacing device 20 need to be removed.

Figure 6A:
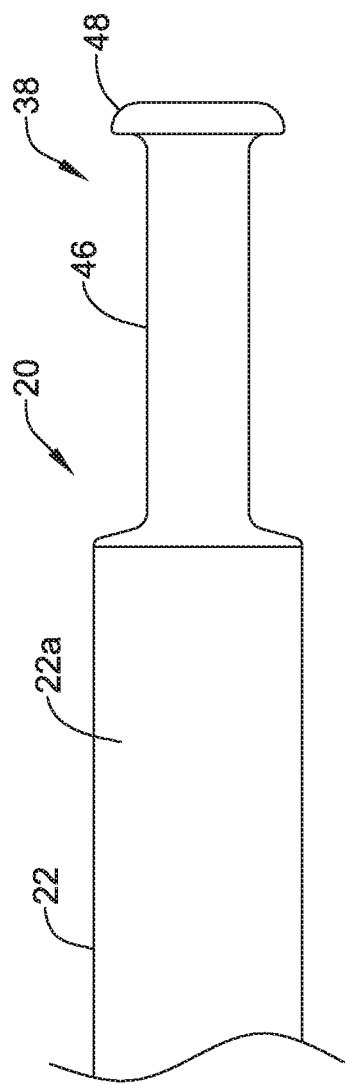
FIGS. 6A-6C are side views of configurations for example proximal members of an implantable leadless pacing device.
Figure 6B:
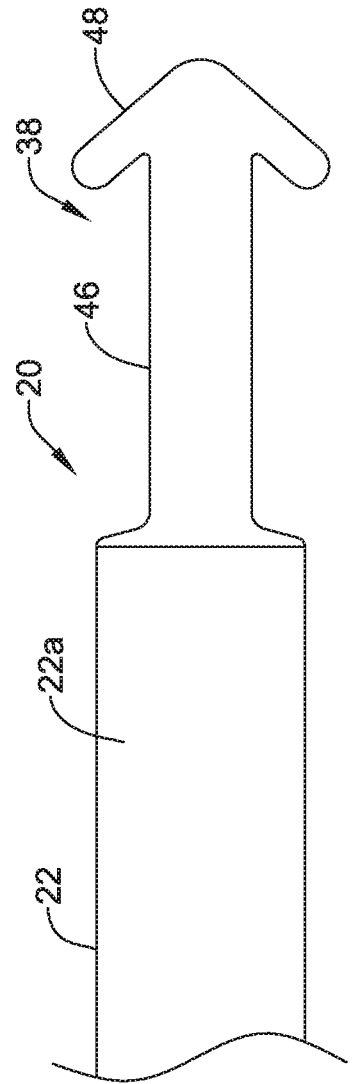
Figure 6C:
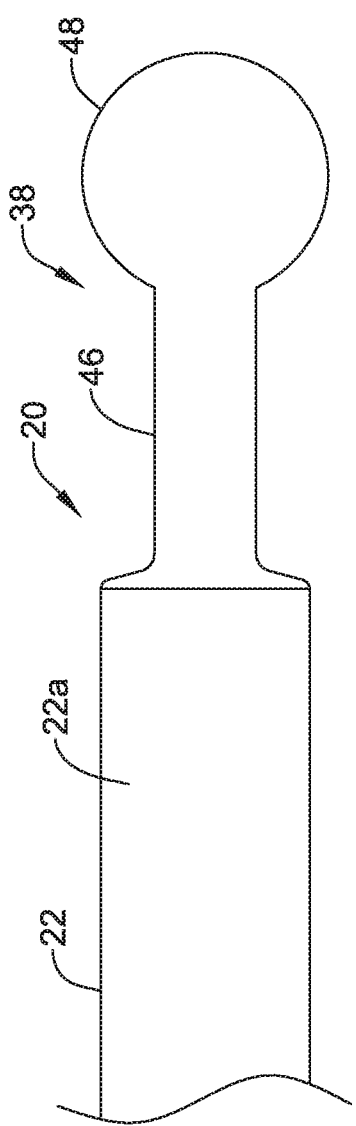

FIGS. 6A-6C depict various illustrative configurations of the proximal member 38. The proximal members 38 may include a flexible or rigid extension 46 extending from a proximal end of the housing 22 and an appendage 48 at a proximal end of the extension 46. Although the configurations of the housing 22 and the extension 46 may vary, in FIGS. 6A-6C the housing 22 and the extensions 46 may be substantially similar with different types of appendages 48 at a proximal end of the extensions 46. FIG. 6A depicts a flat appendage 48 that is substantially perpendicular to the extension 46. FIG. 6B depicts an arrow-shaped appendage 48 that extends radially outward as it extends distally from a proximal end. FIG. 6C depicts a circular or ball shape appendage 48. Although flat-shaped, arrow-shaped, and ball-shaped appendages 48 are depicted in FIGS. 6A-6C, other configurations of the appendage 48 sufficient for grasping or engagement by the retrieval device 78 may be utilized.

As discussed above, the leadless pacing device 20 may be configured to be implanted within the coronary sinus 15 of a patient and thus, sized to fit within the coronary sinus. However, when placed in the coronary sinus 15, the leadless pacing device 20 may occlude or partially occlude the coronary sinus 15 and prevent or limit blood flowing through the coronary sinus 15. Although the blood flowing through the coronary sinus 15 may eventually find other pathways to the heart 10, it may be possible to implant the leadless pacing device 20 while allowing blood to flow past the implanted leadless pacing device 20 by configuring the leadless pacing device 20 to create a fluid pathway when inserted into the coronary sinus 15.

Figure 7:
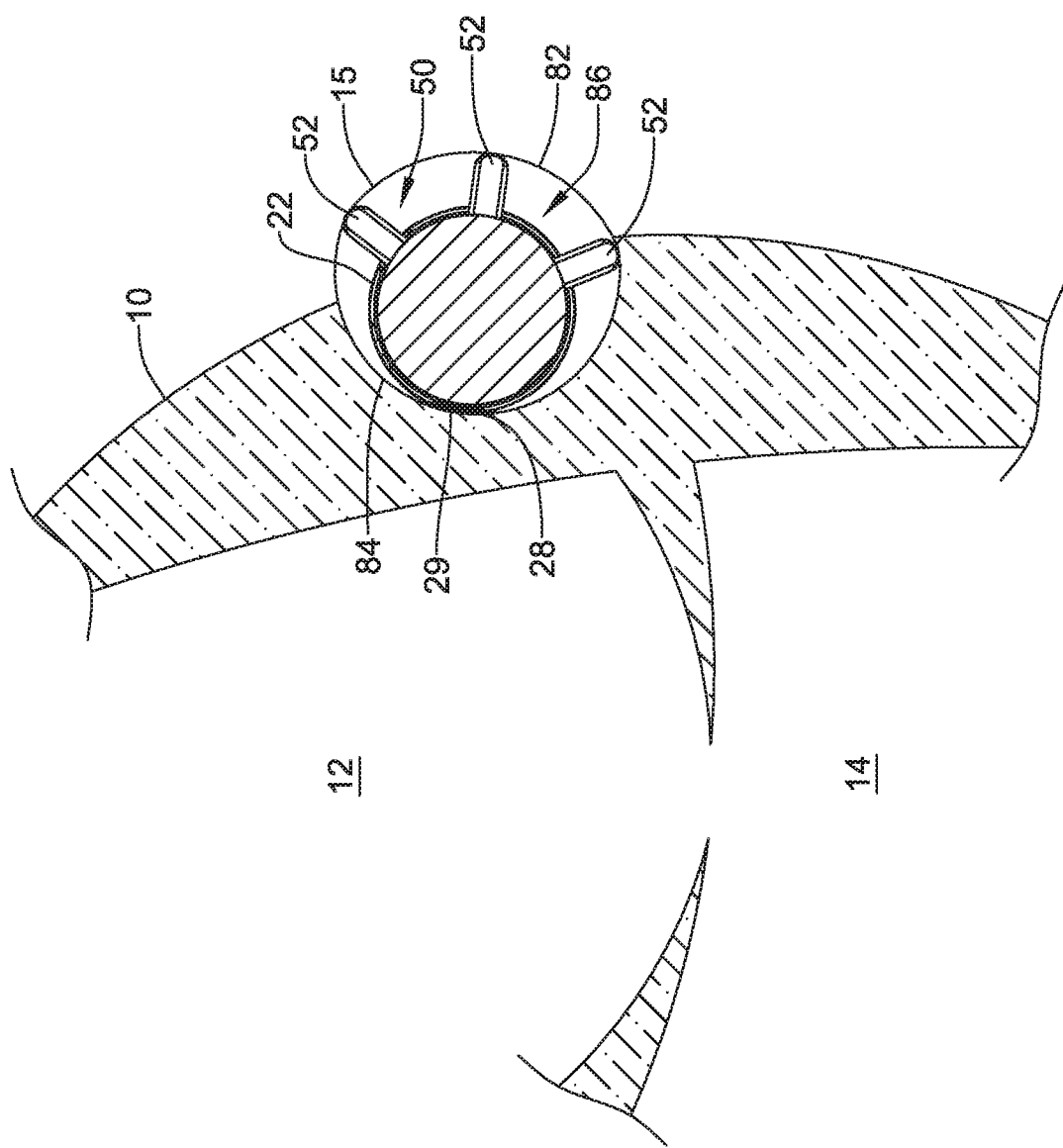
FIG. 7 is a schematic diagram of an example implantable leadless pacing device in a heart.

FIG. 7 depicts one example configuration of a leadless pacing device 20 configured to allow blood to flow past the leadless pacing device 20 while the leadless pacing device 20 is implanted within the coronary sinus 15. As discussed above, the leadless pacing device 20 may include one or more fixing members 50 having one or more anchors 52. As shown in FIG. 7, the anchors 52 of the fixing member 50 may extend radially outward from the housing 22 of the leadless pacing device 20. The fixing member 50 acting on the wall of the coronary sinus 15 may cause the wall of the coronary sinus 15 to expand and create a space 86 between the wall of the coronary sinus 15 and a side of the housing 22 of the leadless pacing device. As a result of creating the space 86, blood may be able to cross the leadless pacing device 20 while the leadless pacing device 20 is implanted in the coronary sinus 15 and flow into the heart 10. Although four (4) anchors are shown in FIG. 7, any other number of anchors may be utilized that is suitable for creating a space 86 for fluid to flow between a side of the housing 22 and a wall of the coronary sinus.

In some instances, the anchors 52 of the fixing member 50 may be asymmetrically positioned or located along a circumference of the housing 22, as shown, in one example, in FIG. 7. In some cases, the positioning of the anchors 52 may be asymmetrically positioned or located around a circumference of the housing 22 such that the exposed portion of the second electrode 28 may be in contact with a second wall portion 84 (e.g., an inner wall portion) of the coronary sinus 15 that also forms a wall of a chamber of a heart (e.g., the left atrium 12, as shown in FIG. 7, or other chamber). In such instances, the anchors 52 may expand at least against a first wall portion 82 (e.g., an outer wall portion) of the coronary sinus 15 that is substantially opposite the second wall portion 84 of the coronary sinus 15 forming a wall of a chamber of the heart 10. Such expansion against the first wall portion 82 may direct the exposed portion 29 of the second electrode 28 against the second wall portion 84 to facilitate good electrical contact between a wall of the heart (e.g., the second wall portion 84) and the second electrode 28. Additionally, the guide wire port 54 (not shown in FIG. 7) may be located on a side of the housing opposite the exposed portion 29 of the second electrode 28 and adjacent the anchors 52 to further facilitate the anchors 52 acting on the first wall portion 82 and good electrical contact between the exposed portion 29 of the second electrode 28 and the second wall portion 84. Although FIG. 7 depicts the position of the second electrode 28, similar configurations may be utilized for ensuring good electrical contact between the other electrodes (e.g., electrodes 26, 30, 32, 34, and 36 and/or other electrodes) of the leadless pacing device 20 and walls of the heart 10.

In some cases, the second wall portion 84 may be adjacent to and/or may include excitable myocardial tissue, whereas the first wall portion 82 may be adjacent to and/or may include fat or pericardium tissue (e.g., tissue that is not excitable myocardial tissue). Excitable myocardial tissue may be tissue of the heart 10 that is responsive to electrical stimulation for the purpose of facilitating operation of the heart 10 (e.g., facilitates capture of the heart 10 in response to electrical stimulation). FIGS. 8A-8B depict another example configuration of a leadless pacing device 20 configured to allow blood to flow past the leadless pacing device 20 while the leadless pacing device 20 is implanted within the coronary sinus 15. As shown in FIGS. 8A-8B, the leadless pacing device 20 may include a recess 88 in the housing 22. The recess 88 may have any dimension and may be at any location on the housing 22 that is suitable for facilitating blood flow across the leadless pacing device 20 when it is implanted within the coronary sinus. Although a single recess 88 is depicted in FIGS. 8A-8B, there may be more than one recess 88 in the housing 22. In some cases, the recess 88 may be an elongated groove (FIG. 8A) and/or an elongated flat surface (FIG. 8B) extending for a length or a portion of a length of the housing 22. Other configurations of the recess 88 are contemplated and any recess suitable for allowing blood to pass the leadless pacing device when implanted in the coronary sinus 15 may be utilized. For example, the recess 88 may be a guide wire lumen, where the guide wire lumen may be configured to allow blood to flow therethrough when a guide wire is not within the guide wire lumen.

When the leadless pacing device 20 having a recess 88 in the housing 22 is implanted within the coronary sinus 15, the space 86 may be created between the housing 22 and the first wall portion 82 of the coronary sinus 15 to facilitate blood flow across the implanted leadless pacing device 20 and into the right atrium 11 of the heart 10. Additionally, the guide wire port 54 (not shown in FIGS. 8A-8B) may be located on a side of the housing 22 opposite the exposed portion 29 of the second electrode 28 and adjacent the recess 88 to facilitate good electrical contact between the exposed portion 29 of the second electrode 28 and/or the first electrode 26 and the second wall portion 84. In instances when the recess 88 may be a guide wire lumen, a proximal opening of the guide wire lumen of the recess 88 may be located at a proximal end of the housing 22 and a distal opening of the guide wire lumen of the recess 88 may be adjacent to and proximal of the guide wire port 54 to allow a guide wire to extend through the recess 88 and into the guide wire port. Although FIGS. 8A-8B depict the position of the second electrode 28, similar configurations may be utilized for ensuring good electrical contact between the other electrodes (e.g., electrodes 26, 30, 32, 34, and 36 and/or other electrodes) of the leadless pacing device 20 and walls of the heart 10. Further, the recess 88 may be utilized as an alternative to or in combination with anchors 52 or other fixing members 50 to maintain good electrical contact between the exposed portion 29 of the second electrode 28 and/or the first electrode 26 and the second wall portion 84 of the heart 10, and create a space between the housing 22 and the first wall portion 82 of the coronary sinus 15 to allow blood to flow past an implanted leadless pacing device 20.

FIGS. 9-12 depict the housing 22 of the leadless pacing device 20 being curved or angled. In some cases, curving or putting an angle in the housing 22 may facilitate delivering the leadless pacing device 20 to the heart 10 and implanting the leadless pacing device 20 in the heart 10. Additionally or alternatively, the housing 22 or at least a portion of the housing 22 may be flexible or bendable. In one example, when the housing 22 is angled or curved, the housing 22 and components therein may be flexible at one or more locations to facilitate straightening the housing 22 (e.g., during delivery through a straight passage and/or at one or more other times) and allowing the housing 22 to return to a curved or angled configuration (e.g., during delivery when the housing 22 is passing through a curved passage, when implanted, and/or at one or more other times). The housing 22 may be configured to passively (e.g., in response to adjacent anatomy) or actively (e.g., in response to controls) move between a straight and a curved or angled configuration.

Figure 9:
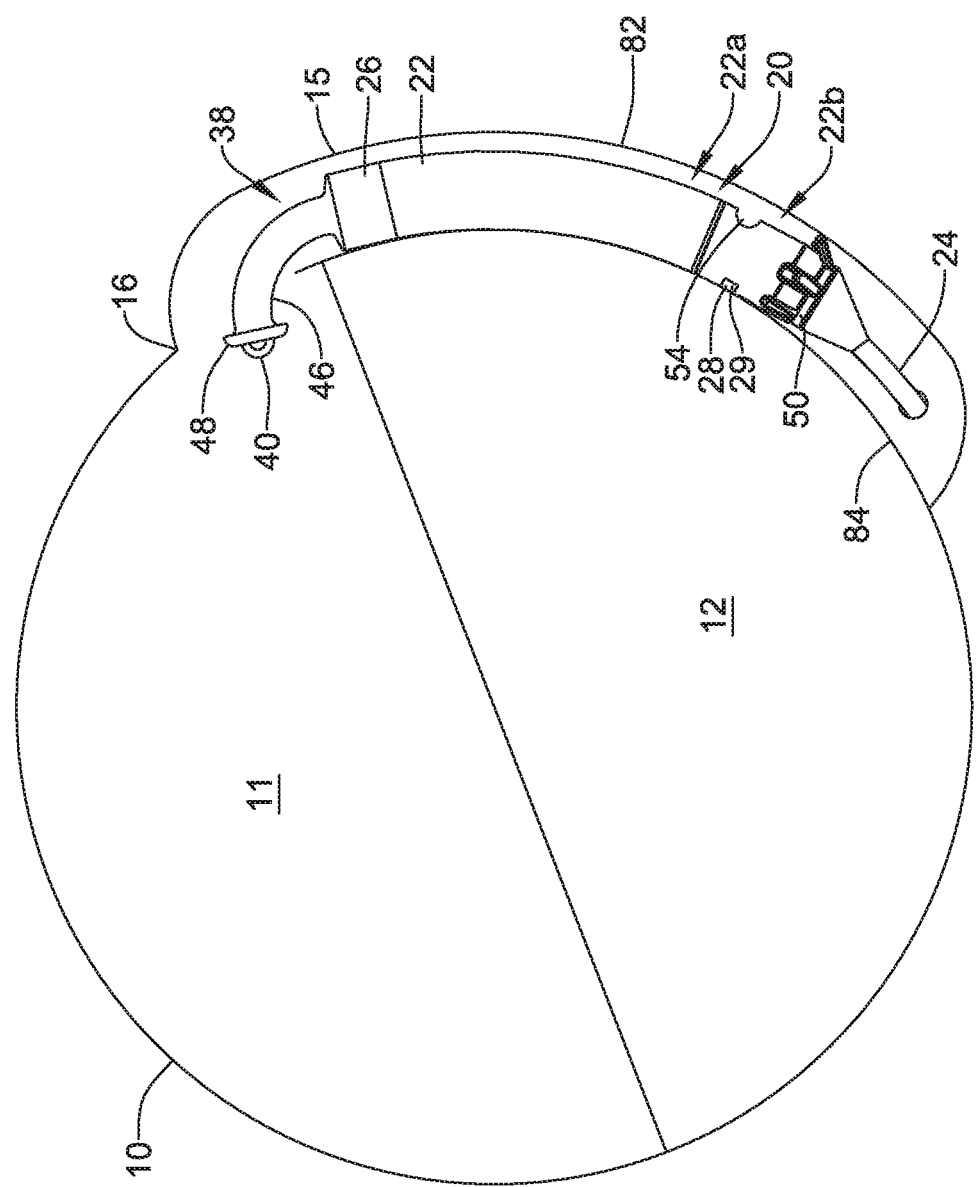
FIG. 9 is a schematic diagram of an example implantable leadless pacing device in a heart.

FIG. 9 is a schematic partial cross-sectional view of the right atrium 11, the left atrium 12, and the coronary sinus 15, where the leadless pacing device 20 is inserted into the coronary sinus 15. The housing 22 of the leadless pacing device 20 may be angled (e.g., the housing 22 may have a smooth-curve or have two or more portions forming an angle less than 180 degrees with respect to one another) along its length and is configured to closely follow a curve of the heart 10. Further, when the exposed portion 29 of the second electrode 28 is on a concave side of the housing 22, the exposed portion 29 of the second electrode 28 may be oriented against and/or facing the second wall portion 84 as the leadless pacing device 20 is inserted into the coronary sinus 15 and the housing 22 having an angled configuration contacts the coronary sinus 15.

Figure 10:
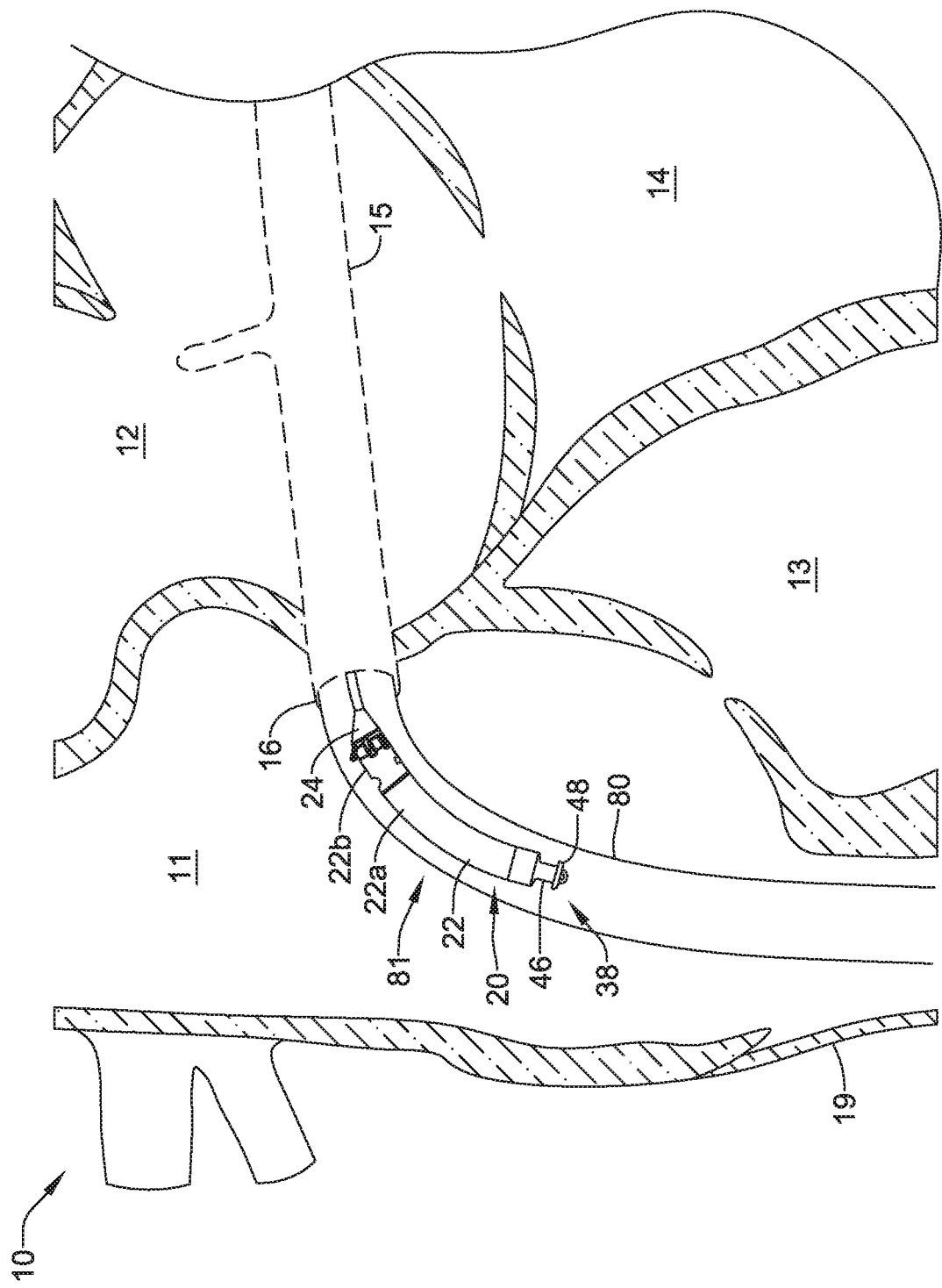
FIG. 10 is a schematic diagram of an example implantable leadless pacing device in a heart.

FIG. 10 is a schematic partial cross-sectional view of the heart with a catheter 80, where the catheter 80 has a bend 81 at a distal end (e.g., at or adjacent a distal tip) to facilitate accessing a passage from the right atrium 11 (e.g., the coronary sinus 15, a right atrial appendage, or other passage in communication with the right atrium 11). In some case, once a leadless pacing device 20 arrives into the right atrium 11 through the inferior vena cava 19, it may be necessary to make a relatively sharp turn into the coronary sinus 15 or other passage. As such, in some cases, the bend 81 (e.g., a curve or turn) at the distal end of the catheter 80 may be positioned for guiding a device from the inferior vena cava 19, into the right atrium 11, and then into the coronary sinus 15. Alternatively, or in addition, the bend 81 (e.g., a curve or turn) at the distal end of the catheter 80 may be positioned for guiding a device from the superior vena cava, into the right atrium 11, and then into the coronary sinus 15. The angle of the bend 81 may depend on the approach path utilized for obtaining access to the coronary sinus 15 and/or on one or more other considerations. Further, a curve or angle in the housing 22 of the leadless pacing device 20 may facilitate following the bend 81 in the catheter 80 and making the turn into the coronary sinus 15, as shown in FIG. 10.

Figure 11:
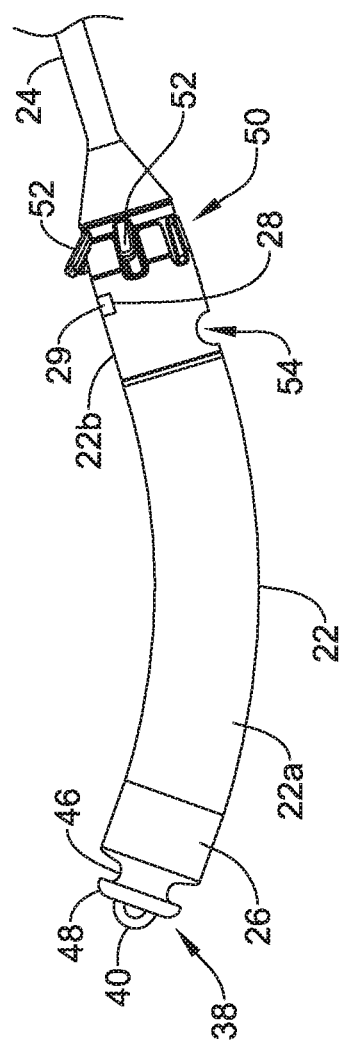
FIG. 11 is a side of an example implantable leadless pacing device.
Figure 12:
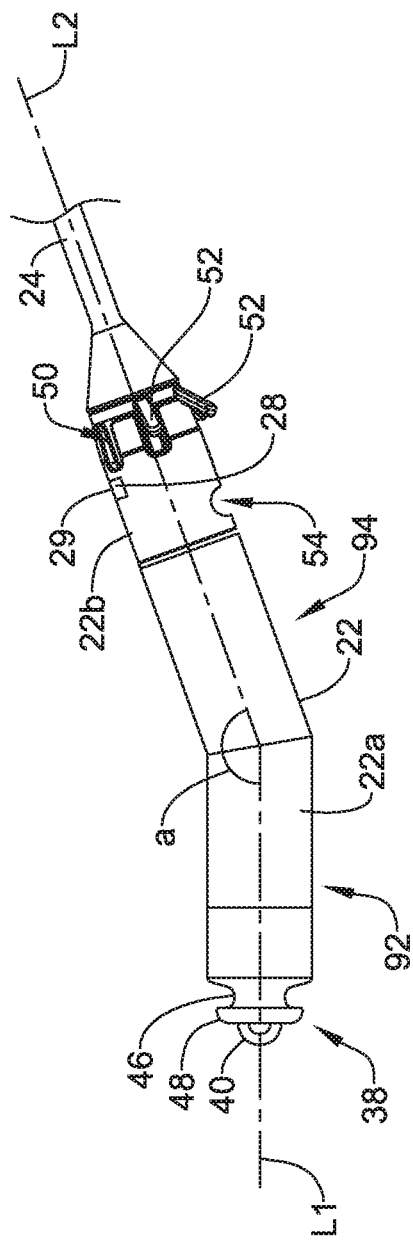
FIG. 12 is a side of an example implantable leadless pacing device.

FIGS. 11 and 12 depict example configurations of the housing 22 of the leadless pacing device 20 having curved or angled configurations. FIG. 11 depicts a housing 22 having a smooth-curve. The smooth-curve may extend along only the first portion 22a of the housing 22, along only the second portion 22b of the housing, or along at least a part of both of the first portion 22a and the second portion 22b of the housing 22. The exposed portion 29 of the second electrode 28 may be located on or adjacent a concave side of the housing 22 and the guide wire port 54 may be located on or adjacent a convex side of the housing 22 to facilitate good contact between the exposed portion 29 of the second electrode 28 and the second wall portion 84 of the coronary sinus 15, for example, similar to as shown in FIG. 9. Additionally, or alternatively, the first electrode 26 may be exposed on or located on the concave side of the housing 22 to facilitate good contact between the first electrode 26 and the second wall portion 84 of the coronary sinus, for example, similar to as shown in FIG. 9.

FIG. 12 depicts a housing 22 having a first angled portion 92 and a second angled portion 94, which may result in the housing 22 having a concave side and a convex side. In some cases, the first angled portion 92 may have a first longitudinal axis L1 and the second angled portion 94 may have a second longitudinal axis L2, where the first longitudinal axis L1 and the second longitudinal axis L2 intersect at an angle, a, that may be less than one hundred-eighty degrees relative to the first linear longitudinal axis L1. The first angled portion 92 and the second angled portion 94 may be formed at any location along a length of the housing 22. For example, the second angled portion 94 may extend from the first angled portion 92 along the first housing portion 22a (as shown in FIG. 12), along the second housing portion 22b, or at a proximal end of the second housing portion 22b and a distal end of the first housing portion 22a. Similar to as discussed above with respect to the housing having a smooth-curve, the exposed portion 29 of the second electrode 28 may be located on or adjacent a concave side of the housing 22 and the guide wire port 54 may be located on or adjacent a convex side of the housing 22 to facilitate good contact between the exposed portion 29 of the second electrode 28 and the second wall portion 84 of the coronary sinus 15, similar to as shown in FIG. 9. Additionally, or alternatively, the first electrode 26 may be exposed on or located on the concave side of the housing 22 to facilitate good contact between the first electrode 26 and the second wall portion 84 of the coronary sinus.

In some embodiments, the leadless pacing device 20 may be delivered to an implant site (e.g., the coronary sinus 15 and/or vessels connected thereto) with a guide catheter, such as catheter 80 of FIG. 13A. The catheter 80 may generally be sized to be able to receive the leadless pacing device 20, a guide wire 96, and a positioning device 98 within a lumen of the catheter 80. When disposed within the catheter 80, the leadless pacing device 20 may be connected to the positioning device 98 by an interlocking mechanism 100. The interlocking mechanism 100 may releasably couple with the proximal member 38 of the housing 22.

To deliver the leadless pacing device 20 to the implant site, the leadless pacing device 20 may be threaded over the guide wire 96, which may have already been positioned within coronary sinus 15 and/or down the great cardiac vein 17 (or other vessel extending from the coronary sinus 15. In some cases, the guide wire 96 may be threaded through the guide wire port 54 and out of a distal end of the distal extension 24, as depicted in FIG. 13A. The catheter 80, including the leadless pacing device 20, may then be advanced over the guide wire 96. Once in position, such as in the coronary sinus 15 of the heart 10, the catheter 80 may be retracted, for example in the direction of arrows 102, thereby exposing the leadless pacing device 20, as depicted in FIG. 13B. The leadless pacing device 20 may be kept in position by positioning device 98. In other instances, instead of or in addition to retracting the catheter 80, the positioning device 98 may be used to push the leadless pacing device 20 out the end of the catheter 80.

In some instances, the positioning device 98 may be semi-flexible, but retain sufficient rigidity to impart force to the leadless pacing device 20 when maneuvered. For instance, once the catheter 80 is in position, and the catheter 80 is then retracted, a user may manipulate the positioning device 98 to impart force on the leadless pacing device 20 through the proximal member 38. In this manner, the user may maneuver the leadless pacing device 20 to a desired location. Once in position, the user may decouple the interlocking mechanism 100 from the proximal member 38, and may retract the guide wire 96 and the catheter 80, including the positioning device 98. Once decoupled, the user may then retract catheter 80 from the body, including positioning device 98.

FIGS. 14A and 14B illustrate the illustrative positioning device 98 and the interlocking mechanism 100. In the example shown in FIGS. 14A and 14B, the positioning device 98 may include a sheath 104. In some instances, the sheath 104 may include one or more structural features that impart a sufficient level of rigidity to allow a user to push, pull, and otherwise move the positioning device 98 and the housing 22 when the positioning device 98 is coupled to the housing 22 via the proximal member 38. For instance, in some embodiments, the sheath 104 may be a braided sheath, or may have a braided covering or inner support member coupled to the sheath 104. In other embodiments, the positioning device 98 may include a coiled wire coupled to the sheath 104.

In the example shown, the interlocking mechanism 100 may include the members 106 which may terminate at one end in prongs 108. In some cases, the members 106 may extend all the way down the sheath 104 and may be manipulated by a user to transition the prongs 108 between an open position (see FIG. 14A) and a closed position (see FIG. 14B). FIG. 14A depicts the prongs 108 in an open configuration and disposed proximate the proximal member 38. When coupling the interlocking device 100, a user may position the prongs 108 in a position close-to or around the proximal member 38. Once in position, the user may manipulate the interlocking members 106 to transition the prongs 108 from the open position into the closed position. FIG. 14B depicts the prongs 108 in the closed position around the proximal member 38.

In the example shown in FIGS. 14A and 14B, the sheath 104 may be able to be moved relative to the interlocking members 106. For example, in the open position, the sheath 104 may not be disposed around the prongs 108 as shown in FIG. 14A. The prongs 108 may be biased such that when the prongs 108 are outside of the sheath 104, the prongs 108 may expand to a greater extent than the diameter of the sheath 104. To transition the prongs 108 to the closed position, a user may simply slide the sheath 104 relative to the interlocking members 106, such as toward the prongs 108. As the sheath 104 is slid toward the prongs 108, at least a portion of the prongs 108 may be compressed by the sheath 104. This compression of the prongs 108 may cause the prongs 108 to transition to the closed position, as depicted in FIG. 14B.

FIGS. 15A-15C depict another embodiment of the positioning device 98 and the interlocking mechanism 100. FIG. 15A depicts the positioning device 98 and the interlocking mechanism 100 disposed proximate the proximal member 38. In these embodiments, the positioning device 98 may include the sheath 104, as described with respect to FIGS. 14A-14B. The interlocking mechanism 100 may include an inflation member 110 and a balloon 112. In some cases, the balloon 112 may have a generally toroidal shape, or any other suitable shape with a hole or recess. To couple to the proximal member 38, a user may position the balloon 112 in an un-inflated state around the proximal member 38, as shown in FIG. 15B. Once the balloon 112 is positioned around the proximal member 38, a user may inflate the balloon 112 by injecting inflation media through the inflation member 110 and into the balloon 112. When the balloon 112 inflates, it expands around the proximal member 38, thereby securing the proximal member 38 to the balloon 112 and thus to the positioning device 98, as depicted in FIG. 15C. When coupled, a user may maneuver the positioning device 98, and consequently the housing 22 attached to the proximal member 38, into a desired position.

FIGS. 16-21 depict an example use of the guide wire 96 and the catheter 80 in the implantation of the leadless pacing device 20 within the heart 10. Although the depicted method includes obtaining access to the patient's heart 10 through the inferior vena cava, access to the heart 10 may also or alternatively be obtained through the superior vena cava and/or other approaches.

In some embodiments, implanting the leadless pacing device 20 within the heart 10 may begin by positioning a guide wire within heart 10, such as the guide wire 96. The guide wire 96 may gain access to the heart 10 through an opening in the patient's skin extending into an artery or vein (e.g., the femoral vein or other vessel) that has been dilated with an introducer or other device having a dilation feature and advancing the guide wire 96 to and/or through the inferior vena cava or other body vessel.

Figure 16:
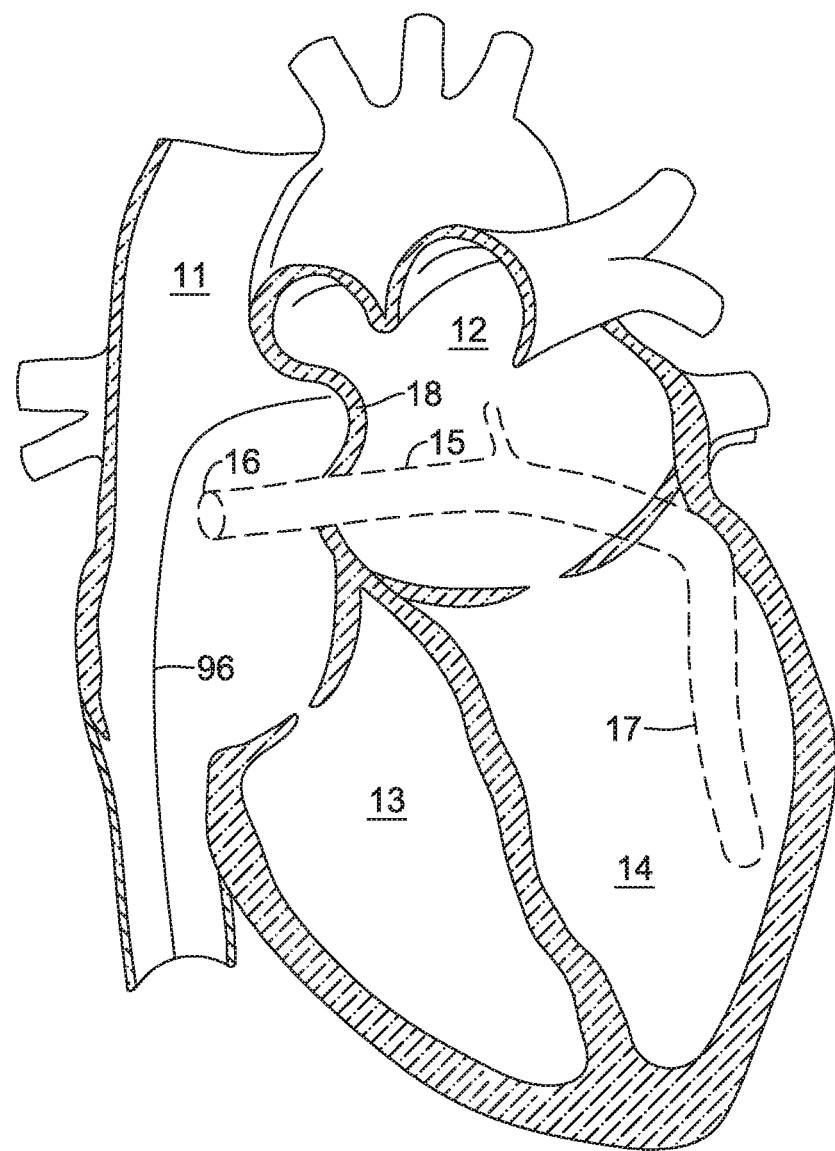
FIGS. 16-21 are a series of schematic diagrams that show delivery and retrieval of an example implantable leadless pacing device into and from a patient's heart.

In some instances, the guide wire 96 may have one or more radiopaque markers disposed on an end of the guide wire 96. Such radiopaque markers may allow for easier viewing of the guide wire 96 through one or more medical imaging systems as the guide wire 96 is maneuvered into position with the heart 10. In some embodiments, the radiopaque markers may be spaced apart from each other by a known distance. In such embodiments, by counting the number of radiopaque markers between two features within the heart 10, a distance may be determined between the two features. In some embodiments, the leadless pacing device 20 may be manufactured in a variety of sizes, or various portions of the leadless pacing device 20, such as the housing 22 and the distal extension 24, may be manufactured in various sizes and lengths. By determining a distance between different features of the patient's heart 10, for instance between the coronary sinus ostium 16 and the septum 18 in the right atrium 11, as depicted in FIG. 16, an appropriate sized housing 22 or distal extension 24 may be selected for the particular patient.

Figure 17:
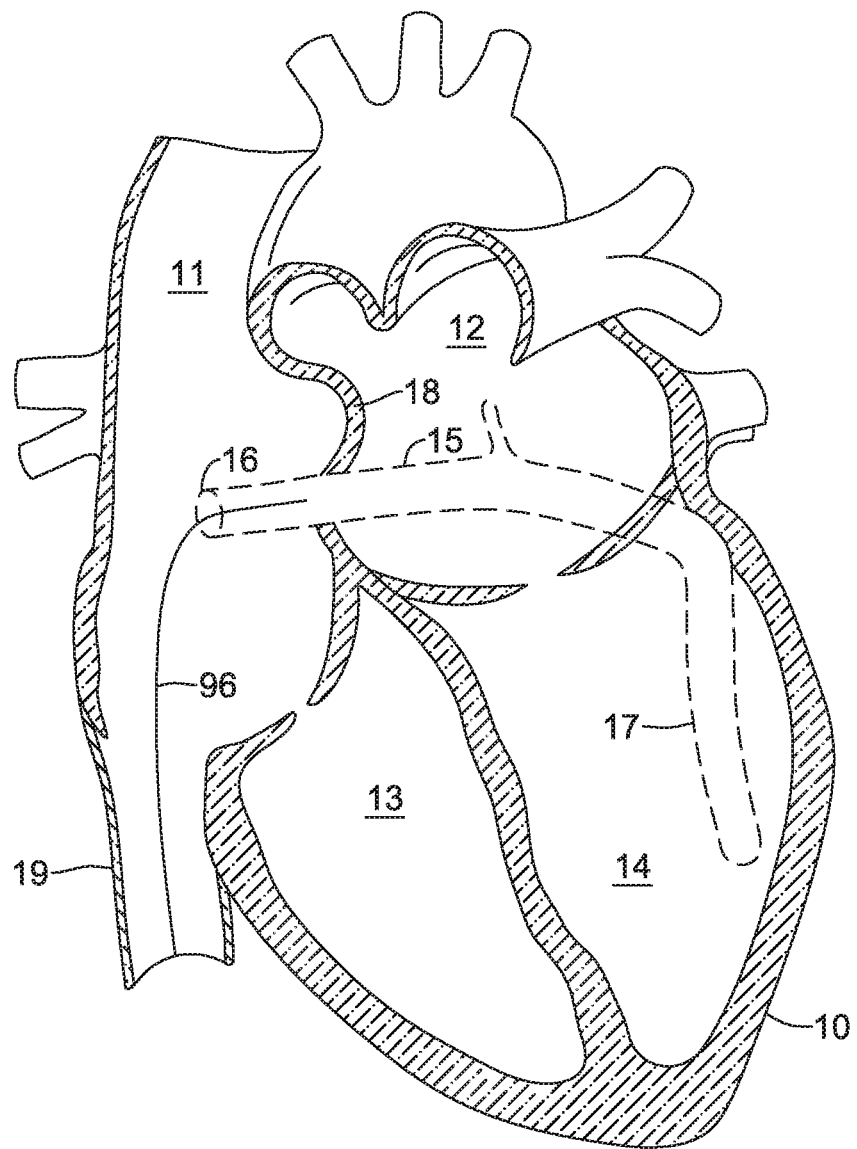
Figure 18:
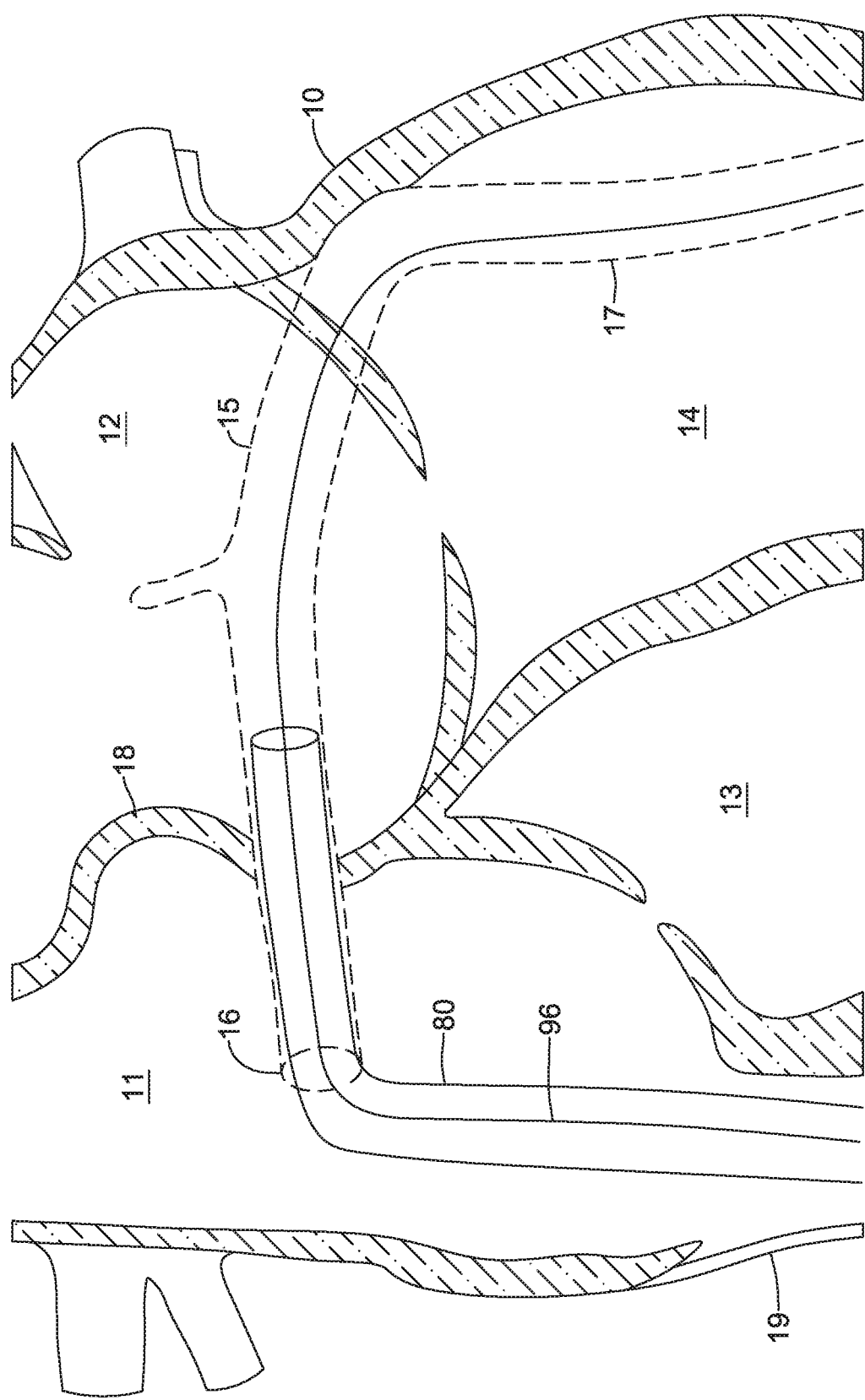

After measuring distances between various features of the heart 10, or in embodiments where such measurements are not needed, the guide wire 96 may then be positioned within the coronary sinus 15, as depicted in FIG. 17. In some instances, the guide wire 96 may be maneuvered all the way through coronary sinus 15 and into the great cardiac vein 17 or other vessel extending from the coronary sinus 15. Once the guide wire 96 is in place, the catheter 80, optionally containing the leadless pacing device 20, may be maneuvered over the guide wire 96 into place within the heart 10. FIG. 18 depicts catheter 80 advanced to and positioned within the coronary sinus 15. In some cases, the catheter 80 may have a dilator feature at or adjacent a distal end (e.g., at or adjacent a distal tip) of the catheter 80. The dilator feature may be configured to engage the ostium 16 of the coronary sinus 15 and dilate and/or cannulate the coronary sinus 15 such that the leadless pacing device 20 may be received therein. In one example, the dilator feature of the catheter 80 may take on the structure of a conical tapered tip, such that advancing the catheter 80 into the coronary sinus 15 expands the inner diameter of the coronary sinus 15. In another example, the dilator feature may be rounded or may have a more abrupt taper than a conical taper. Other dilator feature configurations are contemplated and any configuration suitable for dilating the coronary sinus 15 may be utilized. As such, if the coronary sinus 15 needs to be expanded to receive the leadless pacing device 20, the distal end or distal tip of the catheter 80 may be advanced through the ostium 16 of the coronary sinus 15 to dilate the coronary sinus 15 a suitable amount sufficient to receive the leadless pacing device 20.

Figure 19:
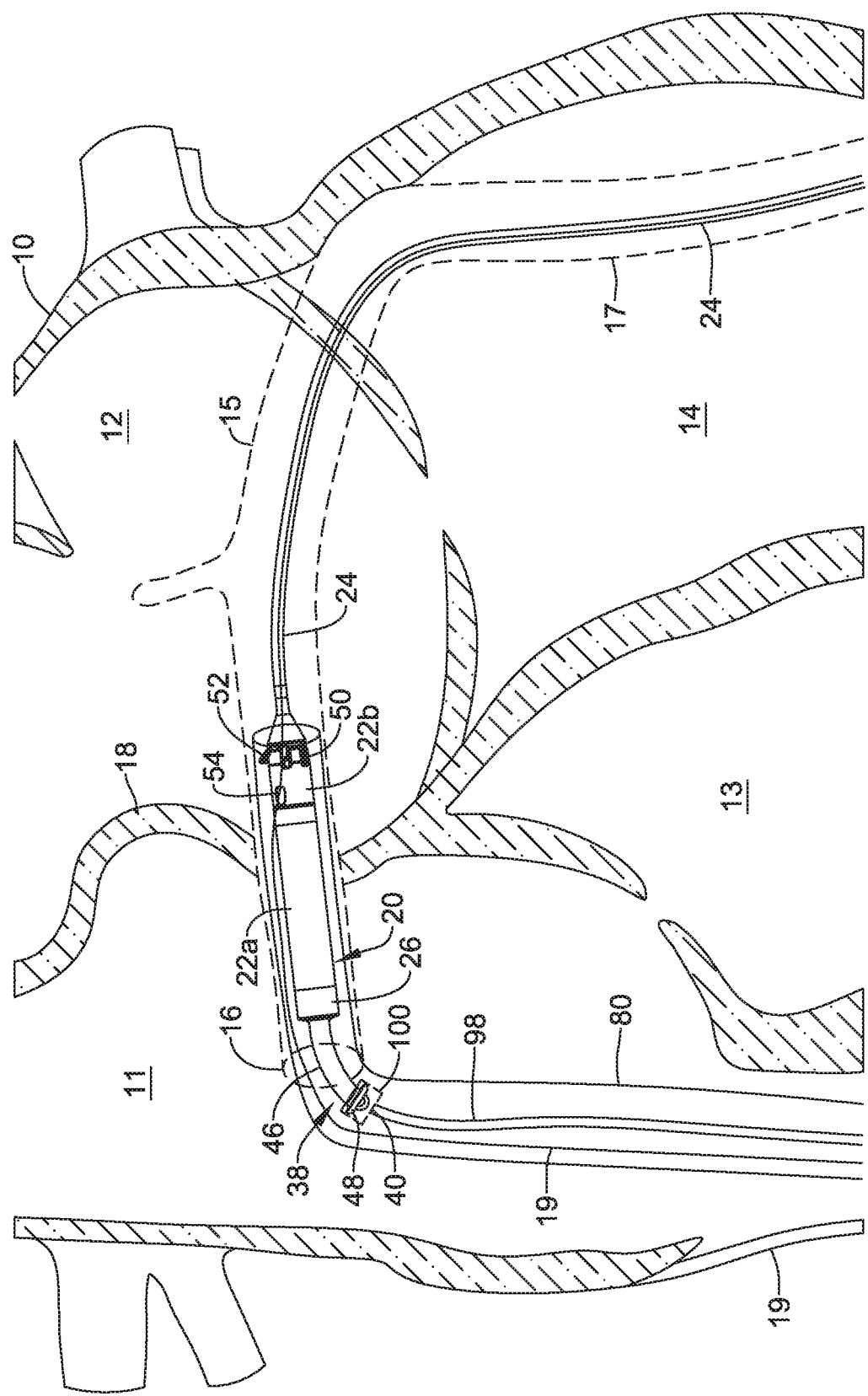

FIG. 19 depicts the guide catheter 80 and the leadless pacing device 20 positioned within the coronary sinus 15 and the proximal member 38 extending proximally out of the coronary sinus 15 into the right atrium 11, with the positioning device 98 and the interlocking mechanism 100 connected to the proximal member 38. The leadless pacing device 20 may be advanced to this position by pushing the leadless pacing device 20 through the catheter 80 and over the guide wire 96 with the positioning device 98 while the interlocking mechanism 100 is connected to the proximal member 38. Alternatively, only one of the catheter 80 or the guide wire 96 may be utilized to position the leadless pacing device 20. Further, it is contemplated that the leadless pacing device 20 may be positioned with neither of the catheter 80 nor the guide wire 96. In some cases, the interlocking mechanism 100 may be connected to or may engage the proximal member 38 until it is positively or intentionally released or disconnected via interacting with a proximal end of the positioning device 98.

In some cases, the leadless pacing device 20 may be adjusted within the coronary sinus 15. In one example, an orientation of the leadless pacing device 20 within the coronary sinus 15 may be adjusted via interacting with a proximal end of the position device 98 to position a flow feature (e.g., the fixing members 50 and/or the recess 88) adjacent a wall (e.g., the first wall portion 82) of the coronary sinus 15 that is spaced from a wall (e.g., the second wall portion 84) of the coronary sinus 15 that forms a wall of a chamber of the patient's heart 10. Such adjustment may facilitate placing one or more electrodes in good contact with the wall of the coronary sinus 15 that forms a wall of a chamber of the patient's heart 10 (e.g., at or adjacent a target site of myocardium in the patient's heart 10).

Figure 20:
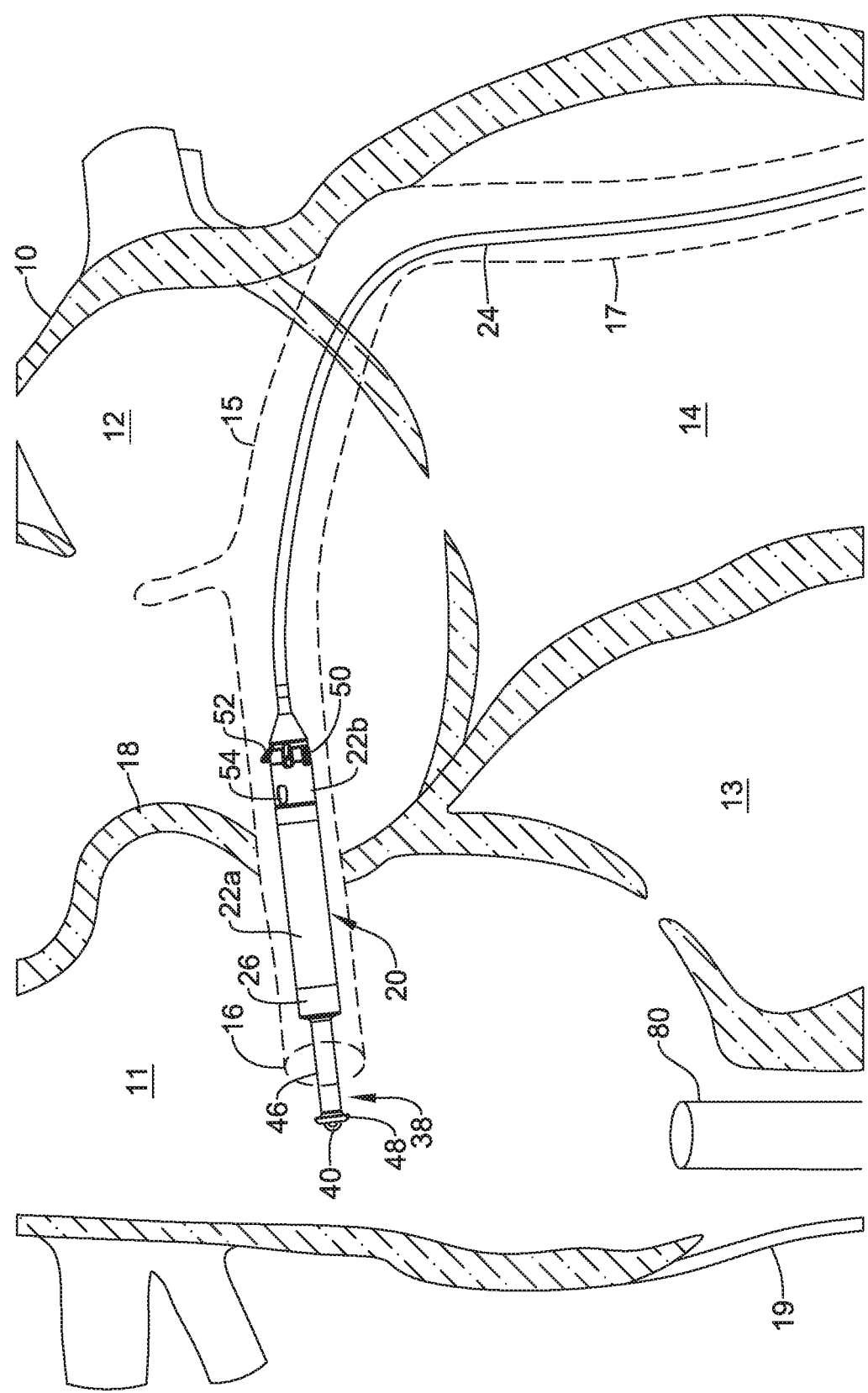

Once the leadless pacing device 20 is in position, the positioning device 98, the catheter 80, and the guide wire 96 may be retracted. FIG. 20 depicts an example of how the leadless pacing device 20 may be positioned after the positioning device 98, catheter 80, and the guide wire 96 have been retracted. Although the housing 22 of the leadless pacing device 20 is depicted as extending along the right atrium 11 and the left atrium 12 in the coronary sinus 15, the housing 22 of the leadless pacing device 20 may be entirely positioned along the right atrium 11 or entirely along the left atrium 12 within the coronary sinus 15. In some instances the housing 22 of the leadless pacing device 20 may be located along both of the right atrium 11 and the left atrium 12 such that the first electrode 26 is in contact with tissue of the right atrium 11 and the second electrode 28 is in contact with tissue of the left atrium 12. In such instances, the leadless pacing device 20 may be programmed to sense and/or pace one or more of the right atrium 11 and left atrium 12 with the respective electrodes 26, 28 or other electrodes due to the electrodes being bipolar.

Figure 21:
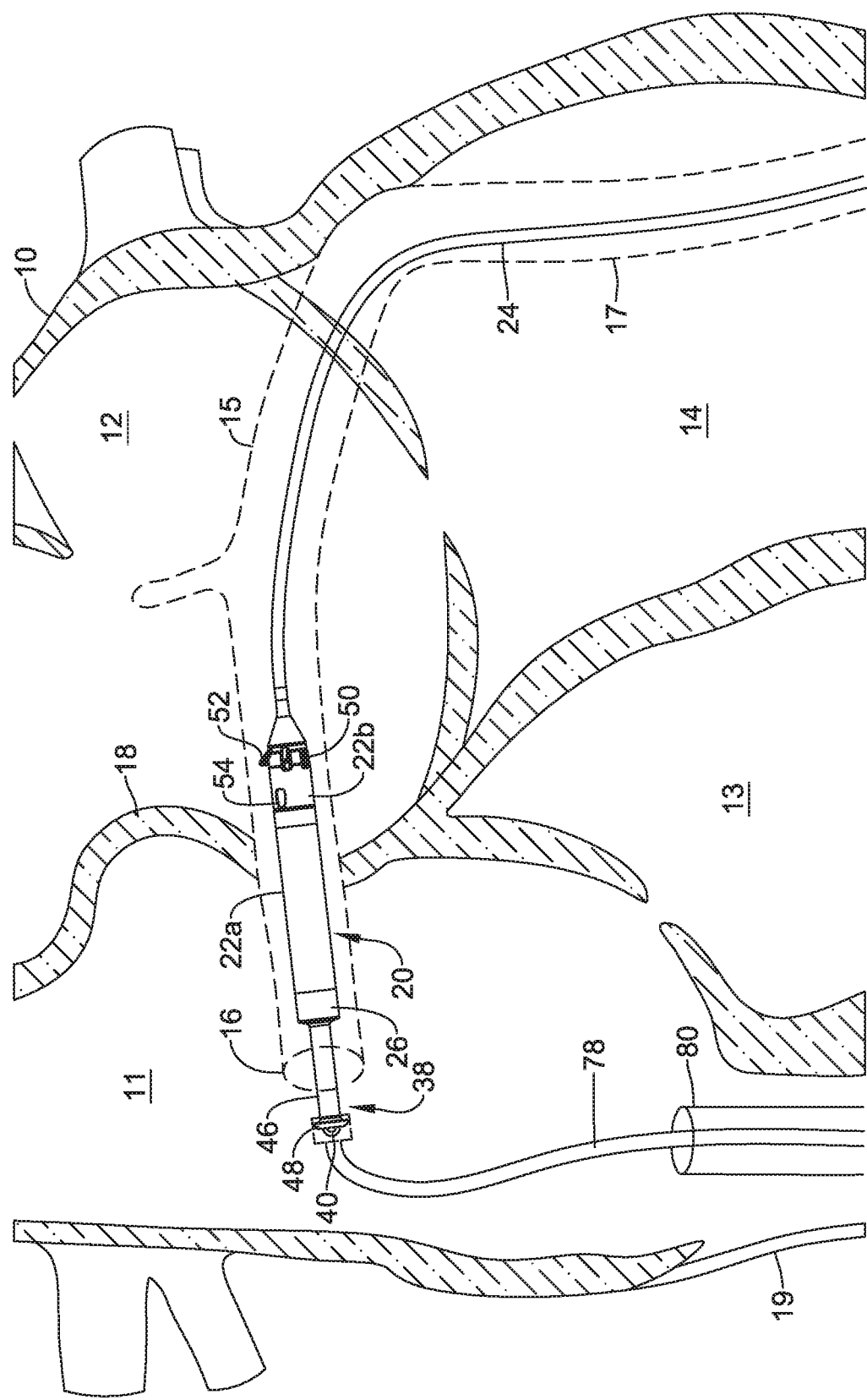

In some cases, the implanted leadless pacing device 20 may be removed from the coronary sinus 15 and/or the positioning of the implanted leadless pacing device 20 may be adjusted. FIG. 21 depicts the retrieval device 78 inserted into the coronary sinus 15 and engaging the proximal member 38 of the leadless pacing device 20. Once the retrieval device 78 has engaged the proximal member 38 of the leadless pacing device 20, the retrieval device 78 and the leadless pacing device 20 may be completely withdrawn from the coronary sinus 15 and the patient's heart 10 and/or repositioned within the coronary sinus 15 and/or the vessels in communication with the coronary sinus 15. In some cases, a sheath (not shown) may be inserted into the coronary sinus 15 and positioned over at least part of the leadless pacing device 20 to articulate the anchors 50 toward a longitudinal axis of the leadless pacing device and facilitate proximal movement of the leadless pacing device 20 within and/or out of the coronary sinus 15.

Those skilled in the art will recognize that the present disclosure may be manifested in a variety of forms other than the specific embodiments described and contemplated herein. For instance, as described herein, various embodiments include one or more modules described as performing various functions. However, other embodiments may include additional modules that split the described functions up over more modules than that described herein. Additionally, other embodiments may consolidate the described functions into fewer modules.

Although various features may have been described with respect to less than all embodiments, this disclosure contemplates that those features may be included on any embodiment. Further, although the embodiments described herein may have omitted some combinations of the various described features, this disclosure contemplates embodiments that include any combination of each described feature. Accordingly, departure in form and detail may be made without departing from the scope and spirit of the present disclosure as described in the appended claims.

What is claimed is:

1. A leadless pacing device comprising:
   a housing configured to be positioned within a coronary sinus;
   a distal extension extending distally of a distal end of the housing, the distal extension is configured to be positioned within a vessel extending from the coronary sinus;
   an electrode supported by the housing;
   a distal electrode supported by the distal extension; and
   a processing module located within an interior space of the housing and electrically coupled to the electrode supported by the housing and the distal electrode supported by the distal extension, wherein the processing module is configured to:
      determine whether an atrial event occurred based on near-field signals sensed using the electrode supported by the housing; and
      determine whether a ventricular event occurred based on near-field signals sensed using the distal electrode.

2. The leadless pacing device of claim 1, wherein the processing module is configured to generate a cardiac stimulation pulse based on the determination of whether an atrial event occurred and the determination of whether a ventricular event occurred.

3. The leadless pacing device of claim 2, wherein the generated cardiac stimulation pulse is generated through the electrode supported by the housing.

4. The leadless pacing device of claim 2, wherein the generated cardiac stimulation pulse is generated through the distal electrode.

5. The leadless pacing device of claim 1, wherein the processing module is configured to determine whether a ventricular event occurred based on far-field signals sensed using the electrode supported by the housing.

6. The leadless pacing device of claim 1, wherein the processing module determines whether an atrial event occurred in a right atrium of a patient's heart based on near-field sensing signals sensed using the electrode supported by the housing.

7. The leadless pacing device of claim 1, wherein the processing module determines whether an atrial event occurred in a left atrium of a patient's heart based on near-field sensing signals sensed using the electrode supported by the housing.

8. The leadless pacing device of claim 1, wherein the electrode supported by the housing is a first electrode, the leadless pacing device further comprising:
   a second electrode supported by the housing.

9. The leadless pacing device of claim 8, wherein the processing module is configured to determine whether an atrial event occurred based on near-field signals sensed using the second electrode.

10. The leadless pacing device of claim 8, wherein the processing module is configured to determine whether an atrial event occurred in a right atrium of a patient's heart based on near-field signals sensed using the first electrode and determine whether an atrial event occurred in a left atrium of the patient's heart based on near-field sensing signal sensed using the second electrode.

11. The leadless pacing device of claim 8, wherein the first electrode is a bipolar electrode and the second electrode is a bipolar electrode.

12. The leadless pacing device of claim 1, wherein the distal extension supports a plurality of electrodes.

13. The leadless pacing device of claim 12, wherein the plurality of electrodes supported by the distal extension comprise a first ring electrode at a distal end of the distal extension and a second ring electrode spaced proximally of the first ring electrode.

14. A leadless pacing device comprising:
  a housing configured to be positioned within a coronary sinus;
  a distal extension connected to a distal end of the housing and extending distally of the housing;
  a lumen extending through the distal extension to a distal guide wire port;
  a first electrode supported by a proximal end of the housing;
  a second electrode supported by a distal end of the housing;
  a proximal guide wire port forming a proximal end of the lumen and extending through a side of the housing at a location between the first electrode and the second electrode;
  a third electrode supported by the distal extension; and
  a processing module located within an interior space of the housing and electrically coupled to the first electrode, the second electrode, and the third electrode, wherein the processing module is configured to:
    determine whether an atrial event occurred based on near-field signals sensed using one or both of the first electrode and the second electrode; and
    determine whether a ventricular event occurred based on near-field signals sensed using the third electrode.

15. The leadless pacing device of claim 14, wherein the processing module is configured to generate a cardiac stimulation pulse based on the determination of whether an atrial event occurred and the determination of whether a ventricular event occurred.

16. The leadless pacing device of claim 14, wherein the processing module is configured to determine whether a ventricular event occurred based on far-field signals sensed using one or both of the first electrode and the second electrode.

17. A method of using a leadless pacing device, the method comprising:
  sensing near-field signals of an atrium of a patient's heart using an electrode supported by a housing of a leadless pacing device located in a coronary sinus of the patient's heart;
  sensing near-field signals of a ventricle of the patient's heart using a distal electrode supported by a distal extension of a leadless pacing device located in a vessel extending from the coronary sinus;
  identifying an atrial cardiac event based on the near-field signals sensed by the electrode supported by the housing; and
  identifying a ventricle cardiac event based on the near-field signals sensed by the distal electrode.

18. The method of claim 17, further comprising:
  generating a cardiac stimulation pulse based on one or both of the identified atrial cardiac event and the identified ventricle cardiac event.

19. The method of claim 17, further comprising:
  sensing far-field signals of a ventricle of the patient's heart using the electrode supported by the housing of the leadless pacing device located in the coronary sinus of the patient's heart; and
  identifying a ventricle cardiac event based on the far-field signals sensed by the electrode supported by the housing.

20. The method of claim 17, wherein the electrode supported by the housing is a first electrode, the method further comprising:
  sensing near-field signals of an atrium of a patient's heart using a second electrode supported by the housing of the leadless pacing device located in the coronary sinus of the patient's heart; and
  identifying if an atrial cardiac event occurred in a right atrium or a left atrium of a patient's heart based on near-field signals sensed by one or both of the first electrode and the second electrode.

* * * * *